US011883435B2

(12) United States Patent
Broxmeyer et al.

(10) Patent No.: US 11,883,435 B2
(45) Date of Patent: Jan. 30, 2024

(54) COMPOSITIONS AND METHODS FOR TREATING A CLINICAL CONDITION THROUGH THE USE OF HEMATOPOIETIC STEM CELLS

(71) Applicant: Indiana University Research and Technology Corporation, Indianapolis, IN (US)

(72) Inventors: Hal Edward Broxmeyer, Indianapolis, IN (US); Maegan Lynn Capitano, Indianapolis, IN (US); Scott Harrison Cooper, Indianapolis, IN (US); Qingchun Cai, Indianapolis, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 667 days.

(21) Appl. No.: 16/487,609

(22) PCT Filed: Jun. 15, 2018

(86) PCT No.: PCT/US2018/037799
§ 371 (c)(1),
(2) Date: Aug. 21, 2019

(87) PCT Pub. No.: WO2018/232272
PCT Pub. Date: Dec. 20, 2018

(65) Prior Publication Data
US 2020/0054681 A1    Feb. 20, 2020

Related U.S. Application Data

(60) Provisional application No. 62/628,637, filed on Feb. 9, 2018, provisional application No. 62/520,140, filed on Jun. 15, 2017.

(51) Int. Cl.
| | |
|---|---|
| A61K 35/28 | (2015.01) |
| A61K 35/51 | (2015.01) |
| A61K 35/14 | (2015.01) |
| A61K 31/198 | (2006.01) |
| A61K 31/661 | (2006.01) |
| A61K 35/44 | (2015.01) |

(52) U.S. Cl.
CPC ............ *A61K 35/28* (2013.01); *A61K 31/198* (2013.01); *A61K 31/661* (2013.01); *A61K 35/14* (2013.01); *A61K 35/44* (2013.01); *A61K 35/51* (2013.01)

(58) Field of Classification Search
CPC ......... A61K 35/28; A61K 35/14; A61K 35/51
See application file for complete search history.

(56) References Cited

U.S. PATENT DOCUMENTS

| | | | |
|---|---|---|---|
| 6,733,746 B2 | 5/2004 | Daley et al. | |
| 7,927,785 B2 | 4/2011 | Milhem et al. | |
| 8,642,255 B2 | 4/2014 | Nicoud et al. | |
| 2006/0182724 A1 | 8/2006 | Riordan | |
| 2013/0040281 A1 | 2/2013 | Dracker | |
| 2015/0159137 A1 | 6/2015 | Sun et al. | |
| 2015/0322405 A1 | 11/2015 | Han | |
| 2016/0095886 A1 | 4/2016 | Ding et al. | |

OTHER PUBLICATIONS

Moldenhauer et al. Optimum storage conditions for cord blood-derived hematopoietic progenitor cells prior to isolation. Bone Marrow Transplantation (2007) 40, 837-842 (Year: 2007).*
Lois et al. The functional modulation of epigenetic regulators by alternative splicing. BMC Genomics 2007, 8:252, p. 1-14 (Year: 2007).*
Mahmud et al. Differential Effects of Epigenetic Modifiers on the Expansion and Maintenance of Human Cord Blood Stem/Progenitor Cells. Biol Blood Marrow Transplant 20 (2014) 480-489 (Year: 2014).*
Posel et al. Density Gradient Centrifugation Compromises Bone Marrow Mononuclear Cell Yield. PLoS One 7(12): e50293. p. 1-10 (Year: 2012).*
Mantel et al. Enhancing Hematopoietic Stem Cell Transplantation Efficacy by Mitigating Oxygen Shock. Cell. 161, p. 1553-1562 (Year: 2015).*
Pamphilon et al. Storage of hemopoietic stem cells. Asian J Transf Sci—vol. 1, Issue 2 (Year: 2007).*
Shao et al. Reactive oxygen species and hematopoietic stem cell senescence. Int J Hematol. Jul. 2011 ; 94(1): 24-32 (Year: 2011).*
Extended European Search Report issued by the European Patent Office, dated Feb. 1, 2021, for European Patent Application No. 18818603.5; 9 pages.
Broxmeyer et al. "The importance of hypoxia and EPHOSS for collection and processing of 54 stem and progenitor cells to understand true physiology/pathology of these cells ex-vivo," Current Opinion in Hematology, Jul. 31, 2015 (Jul. 31, 2015), vol. 22, Iss. 4, pp. 273-278. entire document.
International Search Report and Written Opinion issued by the ISA/US, Commissioner for Patents, dated Sep. 7, 2018, for International Application No. PCT/US2018/037799.
Hal E. Broxmeyer and Louis M. Pelus, Inhibition of DPP4/CD26 and dmPGE2 treatment enhances engraftment of mouse bone marrow hematopoietic stem cells, Blood Cells, Molecules and Diseases 53, 2014; 5 pages.

(Continued)

*Primary Examiner* — Taeyoon Kim
(74) *Attorney, Agent, or Firm* — Faegre Drinker Biddle & Reath LLP

(57) ABSTRACT

Various aspects and embodiments disclosed herein relate generally to the modelling, treatment, reducing resistance to the treatment, prevention, and diagnosis of a condition/disease associated with insufficient quantity and/or quality of hematopoietic stem cells (HSCs) and differentiated blood cells thereof. Embodiments include compositions and methods for treating the condition/disease, comprising the step of providing to a subject at least one therapeutically effective dose of a composition disclosed herein. Other embodiments include methods for generating and/or collecting hematopoietic stem cells from a subject.

7 Claims, 14 Drawing Sheets

(56) References Cited

OTHER PUBLICATIONS

Hal E. Broxmeyer, et al., The importance of hypoxia and extra physiologic oxygen shock/stress for collection and processing of stem and progenitor cells to understand true physiology/pathology of these cells ex vivo, Hematopoiesis, 2015; 6 pages.
International Preliminary Report on Patentability received for PCT Patent Application No. PCT/US2018/037799, dated Dec. 26, 2019, 8 pages.
Sun et al, "Antioxidants cause rapid expansion of human adipose-derived mesenchymal stem cells via CDK and CDK inhibitor regulation," Journal of Biomedical Science, Aug. 1, 2013, vol. 20, Article 53, pp. 1-11.
Charlie R. Mantel, et al., Enhancing Hematopoietic Stem Cell Transplantation Efficacy by Mitigating Oxygen Shock, Cell 161, Jun. 18, 2015, 1553-1565.
Cesar Nombela-Arrieta, et al., Quantitative imaging of haematopoietic stem and progenitor cell localization and hypoxic status in the bone marrow microenvironment, Nature Cell Biology, vol. 15, No. 5, May 2013.
Ahmed Mohyeldin, et al., Oxygen in Stem Cell Biology: A Critical Component of the Stem Cell Niche, Cell Press; 12 pages.
Joel A. Spencer, et al. Direct measurement of local oxygen concentration in the bone marrow of live animals, Research Letter, Apr. 2014, vol. 508; 16 pages.
Kent W. Christopher, II, et al., Cell Surface Peptidase CD26/Dipeptidylpeptidase IV Regulates CXCL12/STromal Cell-Derived Factor-1-Mediated Chemotaxis of Human Cord Blood CD34 + Progenitor Cells, The Journal of Immunology, 2002; 10 pages.
Heather O'Leary, Xuan Ou, Hal E. Broxmeyer, The Role of dipeptidyl peptidase 4 in hematopoiesis and transplantation, Cohematology, vol. 20, No. 4, Jul. 2013; 6 pages.
Nieves Velez de Mendizabal, et al., Modelling the Sitagliptin Effect on Dipeptidyl Peptidase-4 Activity in Adults with Haematological Malignancies After Umbilical Cord Blood Haematopoietic Cell Transplantation, Oct. 9, 2013; 13 pages.
Sherif S. Farag, et al., In Vivo DPP-4 Inhibition to Enhance Engraftment of Single-Unit Cord Blood Transplants in Adults with Hematological Malignancies, Stem Cells and Development, vol. 22, No. 7, 2013; 13 pages.
Kalindi Parmar, et al., Distribution of hematopoietic stem cells in the bone marrow according to regional hypoxia, PNAS, vol. 104, No. 13, Mar. 27, 2007; 6 pages.
Omar S. Aljitawi, et al., Erythropoietin modulation is associated with improved homing and engraftment after umbilical cord blood transplantation, Blood, Dec. 22, 2016, vol. 128, No. 25; 11 pages.
Avital Mendelson, Paul S. Frenette, Hematopoietic stem cell niche maintenance during homeostasis and regeneration, Nature Medicine, vol. 20, No. 8, Aug. 2014; 14 pages.
Jonathan Hoggatt, et al., Prostaglandin E2 enhances hematopoietic stem cell homing survival, and proliferation, Hematopoiesis and Stem Cells, May 28, 2009, vol. 113, No. 22; 12 pages.
Corey Cutler, et al., Prostaglandin-modulated umbilical cord blood hematopoietic stem cell transplantation, The American Society of Hematology, Oct. 24, 2013, vol. 122, No. 17; 8 pages.
X. Huang, et al., Activation of OCT4 enhances ex vivo expansion of human cord blood hematopoietic stem and progenitor cells by regulating HOXB4 expression; 10 pages.
Kent W. Christopherson II, et al., Modulation of Hematopoietic Stem Cell Homing and Engraftment by CD26, Science Mag, Aug. 13, 2004, vol. 305; 5 pages.
Trista E. North, et al., Prostaglandin E2 regulates vertebrate haematopoietic stem cell homeostasis, Research Letters, vol. 447, Jun. 21, 2007; 6 pages.
Pratima Chaurasia, et al., Epigenetic reprogramming induces the expansion of cord blood stem cells, The Journal of Clinical Investigation, vol. 124, No. 6, Jun. 2014; 19 pages.
Sean J. Morrison, David T. Scadden, The bone marrow niche for haematopoietic stem cells, Nature, vol. 505, No. 16, Jan. 2014; 8 pages.
M de Lima, et al., Transplantation of ex vivo expanded cord blood cells using the copper chelator tetraethylenepentamine: a phase I/II clinical trial, Bone Marrow Transplantation, 2008; 8 pages.
Colleen Delaney, et al., Notch-mediated expansion of human cord blood progenitor cells capable of rapid myeloid reconstitution, Nature Medicine, vol. 16, No. 2, Feb. 2010.
Marcos de Lima, MD, et al., Cord-blood Engraftment with Ex Vivo Mesenchymal-Cell Coculture, The New England Journal of Medicine, Dec. 13, 2012; 11 pages.
Mitchell E. Horwitz, et al., Umbilical cord blood expansion with nicotinamide provides long-term multilineage engraftment, The Journal of Clinical Investigation, 2014; 9 pages.
Uday Popat, et al., Enforced fucosylatin of cord blood hematopoietic cells accelerates neutrophil and platelet engraftment after transplantation, The American Society of Hematology; 16 pages.
John E. Wagner, Jr., et al., Phase I/II Trial of StemRegenin-1 Expanded Umbilical Cord Blood Hematopoietic Stem Cells Supports Testing as a Stand-Alone Graft, Stem Cell; 13 pages.
Iman Fares, et al., Pyrimidoindole derivatives are agonists of human hematopoietic stem cell self-renewal, Science Mag, Sep. 19, 2014, vol. 345; 5 pages.
Bibliographical data for WO 2018/232272; 2 pages.
Simon N. Robinson, et al., Non-fucosylated CB CD34+ cells represent a good target for enforced fucosylation to improve engraftment following cord blood transplantation, International Society for Cellular Therapy, 2017; 8 pages.
Anthony E. Boitano, Aryl Hydrocarbon Receptor Antagonists Promote the Expansion of Human Hematopoietic Stem Cells, Science Mag, vol. 329, Sep. 10, 2010; 6 pages.
Umbilical Cord Blood Collection Training, The Cord Blood Bank of Arkansas; 65 pages.
Delayed Umbilical Cord Clamping After Birth, The American College of Obstetricians and Gynecologists, No. 684, Jan. 2017; 6 pages.
Andromachi Scaradavou, et al., Double unit grafts successfully extend the application of umbilical cord blood transplantation in adults with acute leukemia, The American Society of Hematology, vol. 121, No. 5, Jan. 31, 2013; 7 pages.
John E. Wagner, Jr., et al., One-Unit versus Two-Unit Cord-Blood Transplantation for Hematologic Cancers, The New England Journal of Medicine, Oct. 30, 2014; 10 pages.
HE Broxmeyr, et al., Experimental basis of cord blood transplantation, Bone Marrow Transplantation, 2009; 7 pages.
Lujun Xia, et al., Surface fucosylation of human cord blood cells augments binding to P-selectin and E-selectin and enhances engraftment in bone marrow, Blood Journal, Nov. 15, 2004, vol. 104, No. 10; 7 pages.
Karen K. Ballen, et al., Umbilical cord blood transplantation: the first 25 years and beyond, The American Society of Hematology, vol. 122, No. 4, Jul. 25, 2013; 8 pages.
Hal E. Broxmeyer, et al., Human Umbilical Cord Blood as a Potential Source of Transplantable Hematopoietic Stem/Progenitor Cells, PNAS, vol. 86, No. 10, May 15, 1989; 6 pages.
Li-Yi Sun, et al., Antioxidants cause rapid expansion of human adipose-derived mesenchymal stem cells via CDK and CDK inhibitor regulation, Journal of Biomedical Science, 2013; 12 pages.
Juliet N. Barker, et al., Transplantation of 2 partially HLA-matched umbilical cord blood units to enhance engraftment in adults with hematologic malignancy, The American Society of Hematology, Feb. 1, 2005, vol. 105, No. 3; 5 pages.
Bin Guo, et al., Glucocorticoid hormone-induced chromatin remodeling enhances human hematopoietic stem cell homing and engraftment, Nature Medicine, vol. 23, No. 4, Apr. 2017; 7 pages.
Hal E. Broxmeyer, et al., Hematopoietic stem/progenitor cells, generation of induced pluripotent stem cells, and isolation of endothelial progenitors from 21- to 23.5-year cryopreserved cord blood; The American Society of Hematology, May 5, 2011, vol. 117, No. 18; 5 pages.
Hal E. Broxmeyer, et al., Cord Blood Hematopoietic Cell Transplantation; 15 pages.

(56) References Cited

OTHER PUBLICATIONS

Chia-Jung Li, et al., Synergistic Protection of N-Acetylcysteine and Ascorbic Acid 2-Phosphate on Human Mesenchymal Stem Cells Against Mitoptosis, Necroptosis and Apoptosis, Scientific Reports, Apr. 24, 2015; 12 pages.

Cord Blood Banking is About Peace of Mind, https://cordbloodbank.com/collection-and-transportation; 1 page.

Linping Hu, et al., Antioxidant N-acetyl-L-cysteine increases engraftment of human hematopoietic stem cells in immune-deficient mice, The American Society of Hematology, Nov. 13, 2014, vol. 124, No. 20; 4 pages.

Maegan L. Capitano, et al., Mild Heat Treatment Primes Human CD34+ Cord Blood Cells for Migration Toward SDF-1x and Enhances Engraftment in an NSG Mouse Model, Stem Cells; 10 pages.

Hal E. Broxmeyer, The History of cord blood transplantation/biology and perspective for future efforts to enhance the field, Spotlight, Sep. 5, 2017; 10 pages.

Zuzana Tothova, et al., FoxOs Are Critical Mediators of Hematopoietic Stem Cell Resistance to Physiologic Oxidative Stress, Cell 128, Jan. 26, 2007; 15 pages.

Hal E. Broxmeyer, Enhancing the efficacy of engraftment of cord blood for hematopoietic cell transplantation, Transfusion and Apheresis Science 54, 2016; 9 pages.

Charlie Mantel, et al., Mouse hematopoietic cell-targeted STAT3 deletion: stem/progenitor cell defects, mitochondrial dysfunction, ROS overproduction, and a rapid aging-like phenotype, The American Society of Hematology, Sep. 27, 2012, vol. 120, No. 13; 11 pages.

Hal E. Broxmeyer, et al., Dipeptidylpeptidase 4 negatively regulates colony-stimulating factor activity and stress hematopoiesis, Nature Medicine, vol. 18, No. 12, Dec. 2012; 14 pages.

Umbilical Cord Blood Collection Training, The Cord Blood Bank of Arkansas; available as early as Jan. 2016, 65 pages.

Cord Blood Banking is About Peace of Mind, https://cordbloodbank.com/collection-and-transportaion; available as early as Dec. 17, 2019.

\* cited by examiner

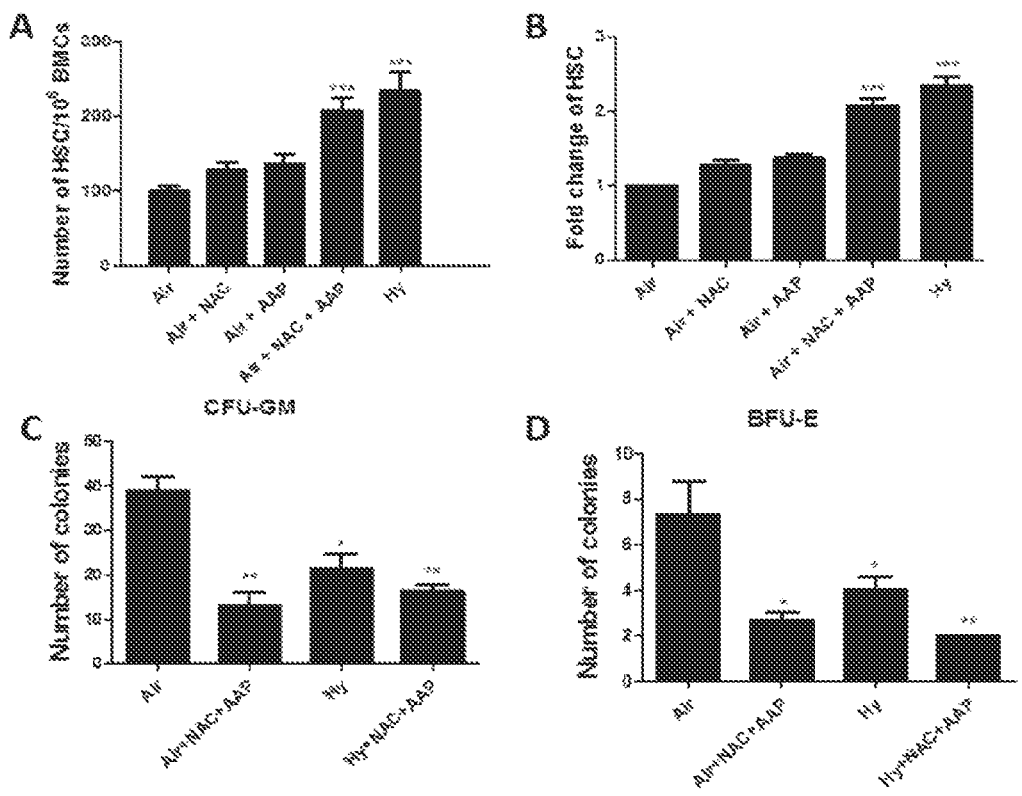
Figure 4A-D

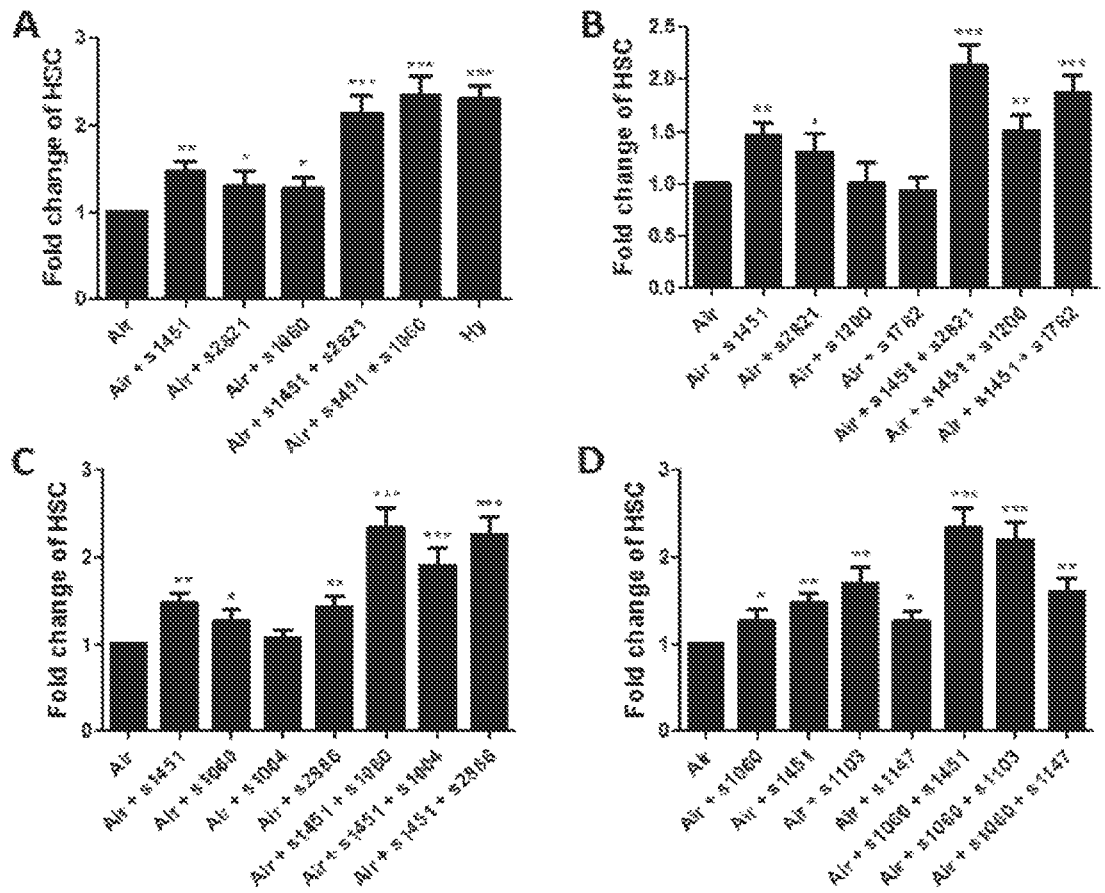
Figure 5A-D

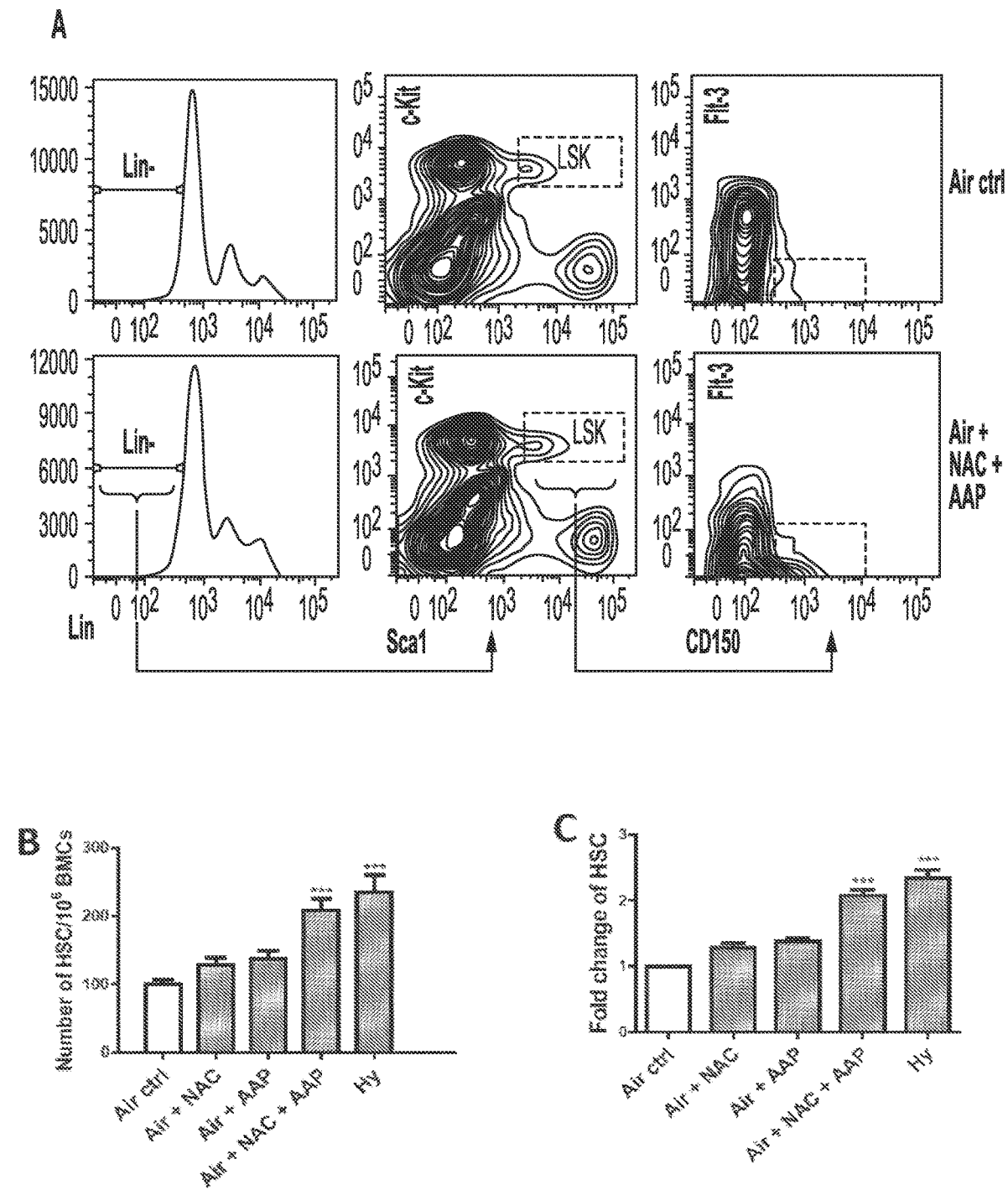
Figure 7A-C

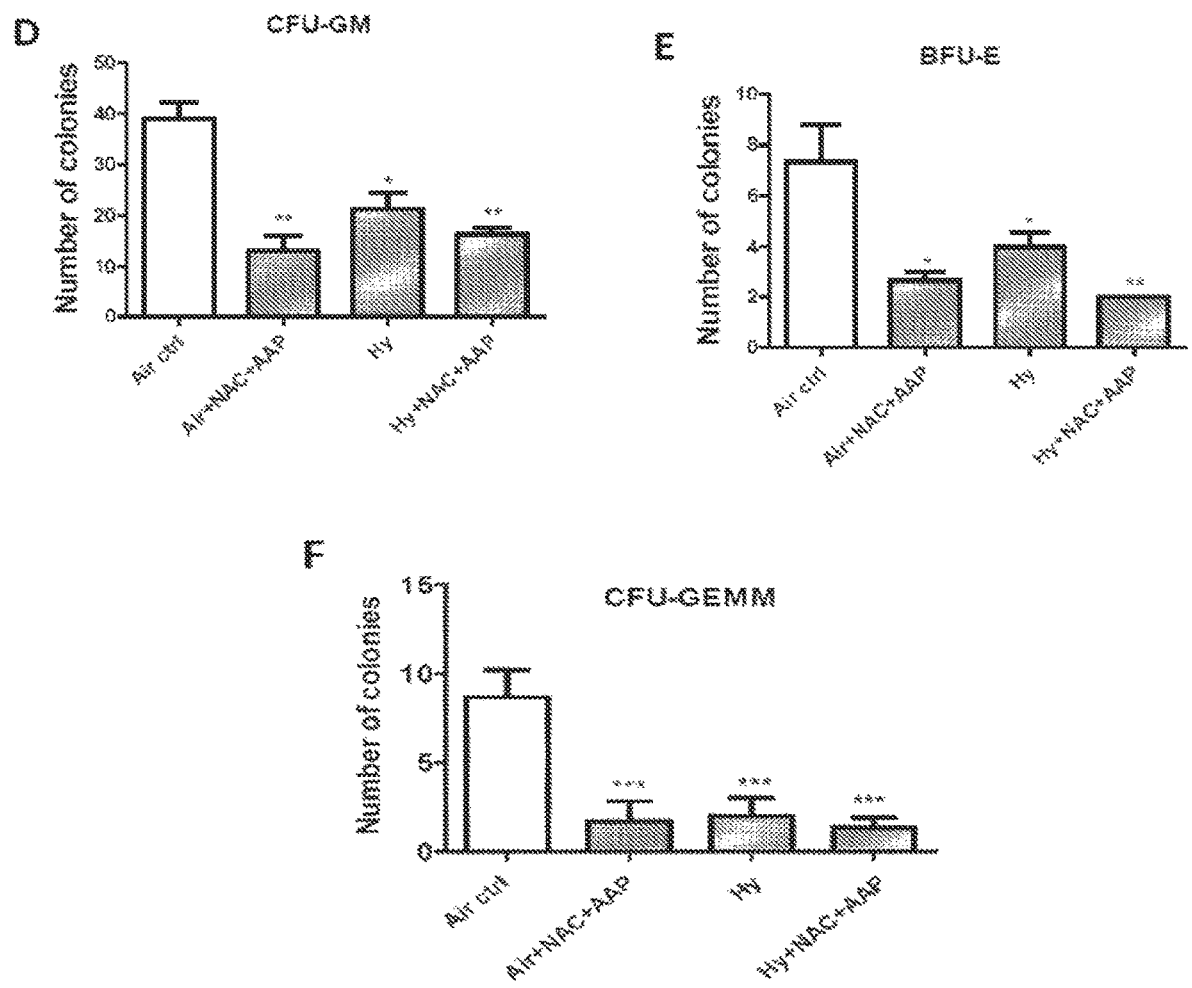
Figure 7D-F

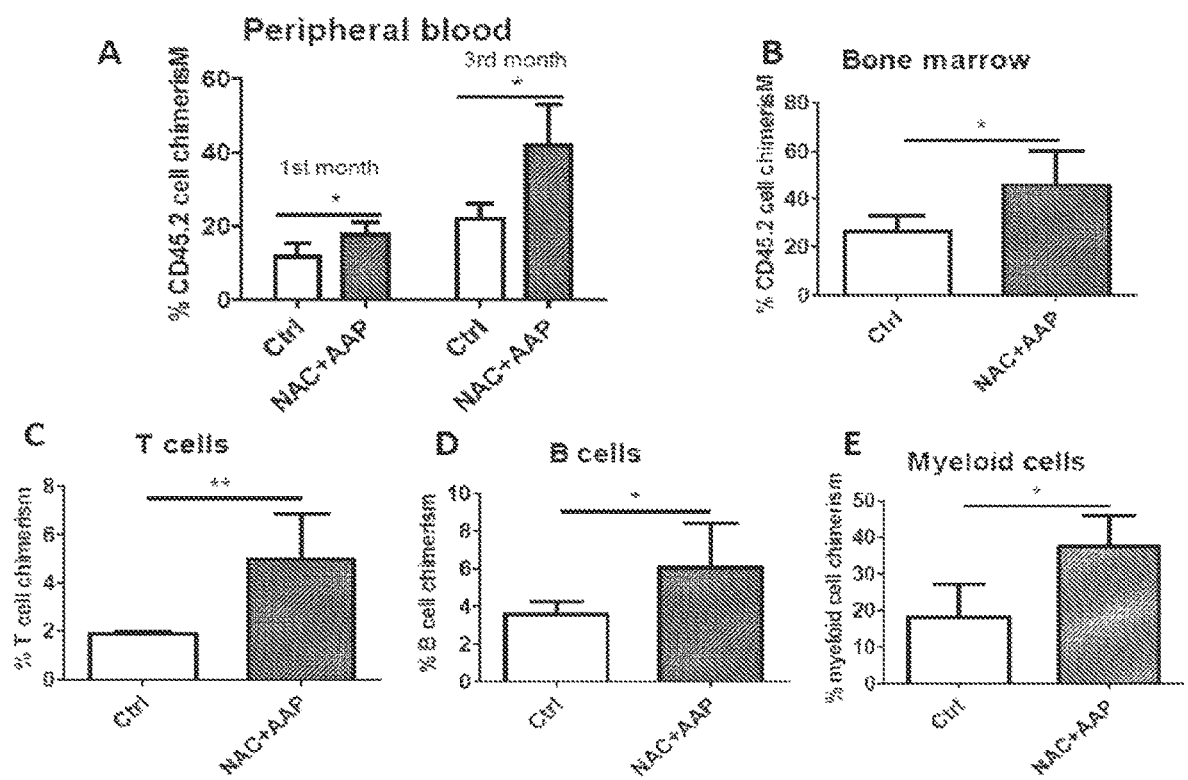
Figure 8A-E

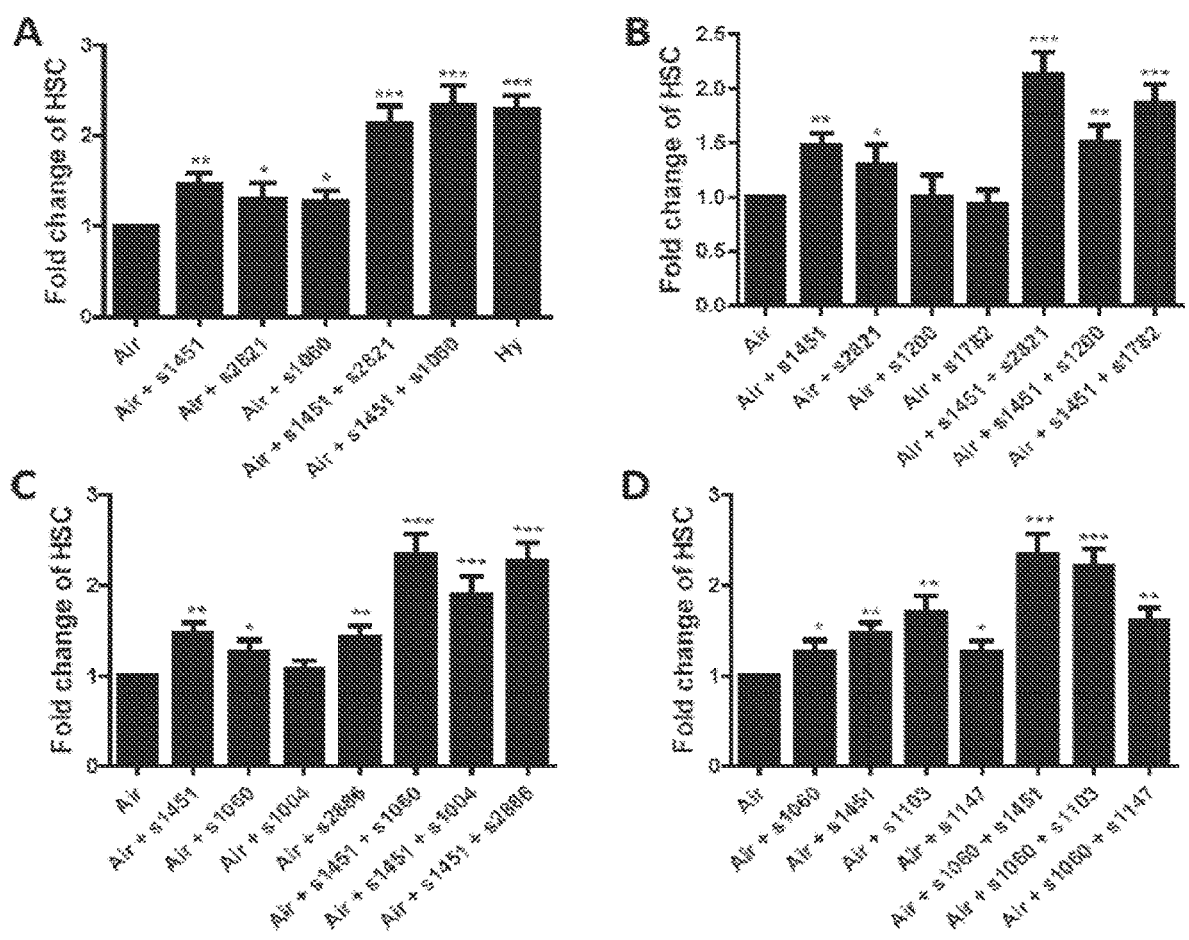
Figure 9A-D

COMPOSITIONS AND METHODS FOR TREATING A CLINICAL CONDITION THROUGH THE USE OF HEMATOPOIETIC STEM CELLS

CROSS REFERENCE TO PRIOR APPLICATIONS

This application is a 35 U.S.C. § 371 U.S. national phase application of International Application Serial No. PCT/US2018/037799, filed Jun. 15, 2018, which claims the benefit of U.S. Provisional Patent Application No. 62/520,140, filed Jun. 15, 2017, and U.S. Provisional Patent Application No. 62/628,637, filed Feb. 9, 2018, each of which is incorporated herein by reference in its entirety.

STATEMENT OF GOVERNMENTAL RIGHTS

This invention was made with government support under HL056416 and DK106846 awarded by the National Institutes to Health. The government has certain rights in the invention.

FIELD

Various aspects and embodiments disclosed herein relate generally to the modelling, treatment, reducing resistance to the treatment, prevention, and diagnosis of a condition/disease associated with insufficient quantity and/or quality of hematopoietic stem cells (HSCs) and differentiated blood cells thereof. Embodiments include compositions and methods for treating the condition/disease, comprising the step of providing to a subject at least one therapeutically effective dose of a composition disclosed herein. Other embodiments include methods for generating and/or collecting hematopoietic stem cells from a subject.

BACKGROUND

Hematopoietic stem cells (HSCs) are the stem cells that give rise to other blood cells through a process called hematopoiesis. HSCs are found, for example, in the bone marrow of adults, particularly in the pelvis, femur, and sternum. They are also found in umbilical cord blood and in peripheral blood. HSCs give rise to both the myeloid and lymphoid lineages of blood cells. Myeloid cells can include, but are not limited to, monocytes, macrophages, neutrophils, basophils, eosinophils, erythrocytes, and megakaryocytes to platelets. Lymphoid cells can include, but are not limited to, T cells, B cells, and natural killer cells.

Hematopoietic stem cell transplantation (HCT) is the transplantation of multipotent hematopoietic stem cells derived generally from bone marrow, peripheral blood, or umbilical cord blood. HCT may be autologous, allogeneic, or syngeneic (from an identical twin). It can be performed on a patient diagnosed with conditions associated with insufficient quantity and/or quality of hematopoietic stem cells (and/or differentiated blood cells thereof). These conditions can include, but are not limited to, cancers (malignant and/or non-malignant), autoimmune diseases, and hereditary skeletal dysplasias. However, HCT is still considered a dangerous procedure with many possible complications such as infections and graft-versus-host diseases (GVHDs). Therefore, development of a new treatment regime that would enhance the effect of HCT on a patient is much needed.

SUMMARY

Embodiments of the instant application relate to compositions, methods for collecting and processing bone marrow, umbilical cord blood, and/or peripheral blood of a subject. In certain embodiments, compositions and methods disclosed herein concern enrichment of hematopoietic stem cells and their use in transplantation. Other embodiments relate to compositions and methods for treating a subject diagnosed with a disease or having a condition contributed to cancers, autoimmune diseases, hereditary skeletal dysplasias, infections, graft-versus-host diseases, and/or any other conditions associated with, induced by, or are already resistant to radiation or chemotherapy.

In some embodiments, compositions disclosed herein include a portion of bone marrow, umbilical cord blood, and/or peripheral blood of a subject; a first antioxidant; and a second antioxidant. Consistent with this embodiment, the first antioxidant and the second antioxidant are independently selected from thiols, vitamin A, vitamin C, vitamin E, uric acids, melatonin, glutathione, n-acetyl-cysteine (NAC), and/or ascorbic acid 2-phosphate (AAP). In certain embodiments, the first antioxidant can be n-acetyl-cysteine (NAC) and the second antioxidant can be selected from thiols, vitamin A, vitamin C, vitamin E, uric acids, melatonin, glutathione, and/or ascorbic acid 2-phosphate (AAP). In other embodiments, the first antioxidant is n-acetyl-cysteine (NAC) and the second antioxidant is ascorbic acid 2-phosphate (AAP). In accordance with these embodiments, the compositions can be placed and/or maintained in ambient air (comprising from about 20% to about 21% $O_2$) or in hypoxia (comprising from about 2.5% to about 3.5% $O_2$); and/or the composition can be placed and/or maintained at a temperature from about 1° C. to about 5° C. or from about 18° C. to about 24° C.

In certain embodiments, the first antioxidant and the second antioxidant are present in the composition in a concentration ratio such that the composition exhibits synergy. The concentration ratio of the first antioxidant and the second antioxidant can be from about 10:1 to about 1:10, from about 9:1 to about 1:9, from about 8:1 to about 1:8, from about 5:1 to about 1:5, from about 2:1 to about 1:2, about 10:1, 5:1, 2:1, 1:1, 1:2, 1:5, 1:10, or any combination(s) thereof. In some embodiments, the compositions can further include at least one agent that alters gene expression. The at least one agent that alters gene expression can include, but is not limited to, a DNA methyltransferase inhibitor, an Aurora kinase inhibitor, a PARP1/2 inhibitor, or any combination thereof.

In any one of embodiments disclosed herein, the portion of bone marrow, umbilical cord blood, and/or peripheral blood comprises hematopoietic stem cells, and the composition comprises hematopoietic stem cells.

In certain embodiments, compositions disclosed herein include a portion of bone marrow, umbilical cord blood, and/or peripheral blood of a subject; and at least one agent that alters gene expression. Consistent with this embodiment, the agent that alters gene expression comprises at least one inhibitor of DNA methylation and/or histone deacetylation; and can include, but is not limited to, a DNA methyltransferase inhibitor, an Aurora kinase inhibitor, a PARP1/2 inhibitor, or any combination thereof. In accordance with these embodiments, the compositions can be placed and/or maintained in ambient air (comprising from about 20% to about 21% $O_2$) or in hypoxia (comprising from about 2.5% to about 3.5% $O_2$); and/or the composition can be placed and/or maintained at a temperature from about 1° C. to about 5° C. or from about 18° C. to about 24° C.

In other embodiments, compositions disclosed herein include a first antioxidant; and a second antioxidant, wherein the composition is added to a portion of bone marrow, umbilical cord blood, and/or peripheral blood of a subject. Consistent with this embodiment, the first antioxidant and the second antioxidant are independently selected from thiols, vitamin A, vitamin C, vitamin E, uric acids, melatonin, glutathione, n-acetyl-cysteine (NAC), and/or ascorbic acid 2-phosphate (AAP). In certain embodiments, the first antioxidant can be n-acetyl-cysteine (NAC) and the second antioxidant can be selected from thiols, vitamin A, vitamin C, vitamin E, uric acids, melatonin, glutathione, and/or ascorbic acid 2-phosphate (AAP). In other embodiments, the first antioxidant is n-acetyl-cysteine (NAC) and the second antioxidant is ascorbic acid 2-phosphate (AAP).

In certain embodiments, the first antioxidant and the second antioxidant are present in the composition in a concentration ratio such that the composition exhibits synergy. The concentration ratio of the first antioxidant and the second antioxidant can be from about 10:1 to about 1:10, from about 9:1 to about 1:9, from about 8:1 to 1:8, from about 5:1 to about 1:5, from about 2:1 to about 1:2, about 10:1, 5:1, 2:1, 1:1, 1:2, 1:5, 1:10, or any combination(s) thereof.

In accordance with these embodiments, the compositions can be placed and/or maintained in ambient air (comprising from about 20% to about 21% $O_2$) or in hypoxia (comprising from about 2.5% to about 3.5% $O_2$); and/or the composition can be placed and/or maintained at a temperature from about 1° C. to about 5° C. or from about 18° C. to about 24° C. In these embodiments, the compositions can further include at least one agent that alters gene expression. The at least one agent that alters gene expression can include, but is not limited to, a DNA methyltransferase inhibitor, an Aurora kinase inhibitor, a PARP1/2 inhibitor, or any combination thereof.

In some embodiments, methods disclosed herein include a method of treating a clinical condition, comprising the step of: providing a subject at least one therapeutically effective dose of any of the compositions disclosed herein. The subject can be diagnosed with a clinical condition selected from and/or comprising cancers, autoimmune diseases, hereditary skeletal dysplasias, infections, graft-versus-host diseases, and/or any other conditions associated with, induced by, or are already resistant to radiation or chemotherapy. Consistent with these embodiments, the subject is diagnosed with a clinical condition comprising acute myeloid leukemia (AML), chronic myeloid leukemia (CIVIL), acute lymphoblastic leukemia (ALL), Hodgkin lymphoma (HL) (relapsed, refractory), Non-Hodgkin lymphoma (NHL) (relapsed, refractory), neuroblastoma, Ewing sarcoma, multiple myeloma, myelodysplastic syndromes, gliomas, solid tumors, thalassemia, sickle cell anemia, aplastic anemia, Fanconi anemia, malignant infantile osteopetrosis, mucopolysaccharidosis, immune deficiency syndromes, infections, graft-versus-host diseases, and/or autoimmune diseases.

In certain embodiments, the methods disclosed herein include a further step of providing the subject at least one additional therapeutically effective dose of any of the compositions disclosed herein; and the composition comprises hematopoietic stem cells that are autologous, allogeneic, or syngeneic, any combination thereof.

In accordance with these embodiments, the methods can include the step of removing the first antioxidant, the second antioxidant, and/or the at least one agent that alters gene expression from the composition.

Yet other embodiments can include methods for collecting bone marrow, cord blood, and/or peripheral blood of a subject in ambient air (comprising from about 20% to about 21% $O_2$) at a temperature from about 1° C. to about 5° C. Consistent with these embodiments, the methods further include the step of isolating hematopoietic stem cells (HSCs). In certain embodiments, the bone marrow, cord blood, and/or peripheral blood can be placed and/or maintained in ambient air (comprising from about 20% to about 21% $O_2$) and at a temperature from about 3° C. to about 5° C. In accordance with these embodiments, the isolated populations of HSCs can include $CD34^+CD38^-$ HSCs.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 4A. Graph illustrating the effect of antioxidants on the number of mouse bone marrow HSCs collected in ambient air. The number of HSCs in 1 million mouse bone marrow cells (BMCs) collected in ambient air in the presence of 1 mM NAC and/or 0.22 mM AAP is shown. The number of mouse bone marrow HSCs collected in hypoxia (about 3% $O_2$) was used as a control. *** p<0.001. n=5, 10 mice.

FIG. 4B. Graph illustrating the effect of antioxidants on the number of mouse bone marrow HSCs collected in ambient air. The fold change of mouse bone marrow HSCs collected in ambient air in the presence of 1 mM NAC and/or 0.22 mM AAP is shown. The fold increase of mouse bone marrow HSCs collected in hypoxia (about 3% $O_2$) was used as a control. *** p<0.001. n=5, 10 mice.

FIG. 4C. Graph illustrating the effect of antioxidants on the number of mouse bone marrow colony forming units-granulocyte macrophages (CFU-GMs). CFU-GMs were collected in ambient air or in hypoxia (about 3% $O_2$) in the presence of 1 mM NAC and/or 0.22 mM AAP. * p<0.05, ** p<0.01. n=5, 10 mice.

FIG. 4D. Graph illustrating the effect of antioxidants on the number of mouse bone marrow burst forming units-erythroids (BFU-Es). BFU-Es were collected in ambient air or in hypoxia (about 3% $O_2$) in the presence of 1 mM NAC and/or 0.22 mM AAP. * p<0.05, ** p<0.01. n=5, 10 mice.

FIG. 5A. Graph illustrating the effect of epigenetic inhibitors on the number of mouse bone marrow HSCs. The fold change of mouse bone marrow HSCs collected in ambient air in the presence of 10 μM s1451 (Aurora kinase inhibitor), 10 μM s2821 (DNA methyltransferase inhibitor) and/or 10 μM s1060 (PARP1/2 inhibitor) is shown. The fold change of mouse bone marrow HSCs collected in hypoxia (about 3% $O_2$) was used as a positive control. * p<0.05,  p<0.01, * p<0.001. n=3, 7 mice.

FIG. 5B. Graph illustrating the effect of epigenetic inhibitors on the number of mouse bone marrow HSCs. The fold change of mouse bone marrow HSCs collected in ambient air in the presence of 10 μM s1451 (Aurora kinase inhibitor), 10 μM s2821 (DNA methyltransferase inhibitor), 10 μM s1200 (DNA methyltransferase inhibitor), and/or 10 μM s1782 (DNA methyltransferase inhibitor) is shown. * p<0.05,  p<0.01, * p<0.001. n=3, 7 mice.

FIG. 5C. Graph illustrating the effect of epigenetic inhibitors on the number of mouse bone marrow HSCs. The fold change of mouse bone marrow HSCs collected in ambient air in the presence of 10 μM s1451 (Aurora kinase inhibitor), 10 μM s1060 (PARP1/2 inhibitor), 10 μM s1004 (PARP1/2 inhibitor), and/or 10 μM s2886 (PARP1/2 inhibitor) is shown. * p<0.05,  p<0.01, * p<0.001. n=3, 7 mice.

FIG. 5D. Graph illustrating the effect of epigenetic inhibitors on the number of mouse bone marrow HSCs. The fold change of mouse bone marrow HSCs collected in ambient air in the presence of 10 μM s1060 (PARP1/2 inhibitor), 10 μM s1451 (Aurora kinase inhibitor), 10 μM s1103 (Aurora kinase inhibitor), and/or 10 μM s1147 (Aurora kinase inhibitor) is shown. * p<0.05,  p<0.01, * p<0.001. n=3, 7 mice.

FIG. 7A. Contour plots of mouse bone marrow HSCs illustrating the effect of treatment with antioxidants (1 mM NAC and 0.22 mM AAP) or vehicle.

FIG. 7B. Graph illustrating the effect of antioxidants on the number of mouse bone marrow HSCs collected in ambient air. The number of HSCs in 1 million mouse bone marrow cells (BMCs) collected in ambient air in the presence of 1 mM NAC and/or 0.22 mM AAP is shown. The number of mouse bone marrow HSCs collected in hypoxia (about 3% $O_2$) was used as a positive control. * p<0.05,  p<0.01, * p<0.001.

FIG. 7C. Graph illustrating the effect of antioxidants on the number of mouse bone marrow HSCs collected in ambient air. The fold change of HSCs collected in ambient air in the presence of 1 mM NAC and/or 0.22 mM AAP is shown. The fold increase of mouse bone marrow HSCs collected in hypoxia (about 3% $O_2$) was used as a positive control. * p<0.05,  p<0.01, * p<0.001.

FIG. 7D. Graph illustrating the effect of antioxidants on the number of mouse bone marrow colony forming units-granulocyte macrophages (CFU-GMs). CFU-GMs were collected in ambient air or in hypoxia (about 3% $O_2$) in the presence of 1 mM NAC and/or 0.22 mM AAP. * p<0.05,  p<0.01, * p<0.001.

FIG. 7E. Graph illustrating the effect of antioxidants on the number of mouse bone marrow burst forming units-erythroids (BFU-Es). BFU-Es were collected in ambient air or in hypoxia (about 3% $O_2$) in the presence of 1 mM NAC and/or 0.22 mM AAP. * p<0.05,  p<0.01, * p<0.001.

FIG. 7F. Graph illustrating the effect of antioxidants on the number of mouse bone marrow colony forming units-granulocyte, erythroid, macrophage, megakaryocyte (CFU-GEMMs). CFU-GEMMs were collected in ambient air or in hypoxia (about 3% $O_2$) in the presence of 1 mM NAC and/or 0.22 mM AAP. * p<0.05,  p<0.01, * p<0.001.

FIG. 8A. Graph illustrating percent mouse antioxidant treated or vehicle control treated CD45.2 cells in the peripheral blood of sub-lethally irradiated F1 mice (CD45.1$^+$CD45.2$^+$) at 1 or 3 months after transplantation. * p<0.05,  p<0.01, * p<0.001. n=5.

FIG. 8B. Graph illustrating percent mouse antioxidant treated or vehicle control treated CD45.2 cells in the bone marrow of sub-lethally irradiated F1 mice (CD45.1$^+$CD45.2$^+$) at 3 months after transplantation. * p<0.05,  p<0.01, * p<0.001. n=5.

FIG. 8C. Graph illustrating percent mouse CD45.2$^+$ T cells in the bone marrow of sub-lethally irradiated F1 mice (CD45.1$^+$CD45.2$^+$) at 3 months after transplantation. * p<0.05,  p<0.01, * p<0.001. n=5.

FIG. 8D. Graph illustrating percent mouse CD45.2$^+$ B cells in the bone marrow of sub-lethally irradiated F1 mice (CD45.1$^+$CD45.2$^+$) at 3 months after transplantation. * p<0.05,  p<0.01, * p<0.001. n=5.

FIG. 8E. Graph illustrating percent mouse CD45.2$^+$ myeloid cells in the bone marrow of sub-lethally irradiated F1 mice (CD45.1$^+$CD45.2$^+$) at 3 months after transplantation. * p<0.05,  p<0.01, * p<0.001. n=5.

FIG. 9A. Graph illustrating the effect of epigenetic inhibitors on the number of mouse bone marrow HSCs. The fold change of mouse bone marrow HSCs collected in ambient air in the presence of 10 μM s1451 (Aurora kinase inhibitor), 10 μM s2821 (DNA methyltransferase inhibitor) and/or 10 μM s1060 (PARP1/2 inhibitor) is shown. The fold change of mouse bone marrow HSCs collected in hypoxia (about 3% O$_2$) was used as a positive control. * p<0.05,  p<0.01, * p<0.001. n=3, 7 mice.

FIG. 9B. Graph illustrating the effect of epigenetic inhibitors on the number of mouse bone marrow HSCs. The fold change of mouse bone marrow HSCs collected in ambient air in the presence of 10 μM s1451 (Aurora kinase inhibitor), 10 μM s2821 (DNA methyltransferase inhibitor), 10 μM s1200 (DNA methyltransferase inhibitor), and/or 10 μM s1782 (DNA methyltransferase inhibitor) is shown. * p<0.05,  p<0.01, * p<0.001. n=3, 7 mice.

FIG. 9C. Graph illustrating the effect of epigenetic inhibitors on the number of mouse bone marrow HSCs. The fold change of mouse bone marrow HSCs collected in ambient air in the presence of 10 μM s1451 (Aurora kinase inhibitor), 10 μM s1060 (PARP1/2 inhibitor), 10 μM s1004 (PARP1/2 inhibitor), and/or 10 μM s2886 (PARP1/2 inhibitor) is shown. * p<0.05,  p<0.01, * p<0.001. n=3, 7 mice.

FIG. 9D. Graph illustrating the effect of epigenetic inhibitors on the number of mouse bone marrow HSCs. The fold change of mouse bone marrow HSCs collected in ambient air in the presence of 10 μM s1060 (PARP1/2 inhibitor), 10 μM s1451 (Aurora kinase inhibitor), 10 μM s1103 (Aurora kinase inhibitor), and/or 10 μM s1147 (Aurora kinase inhibitor) is shown. * p<0.05,  p<0.01, * p<0.001. n=3, 7 mice.

DEFINITIONS

Figure 1A:
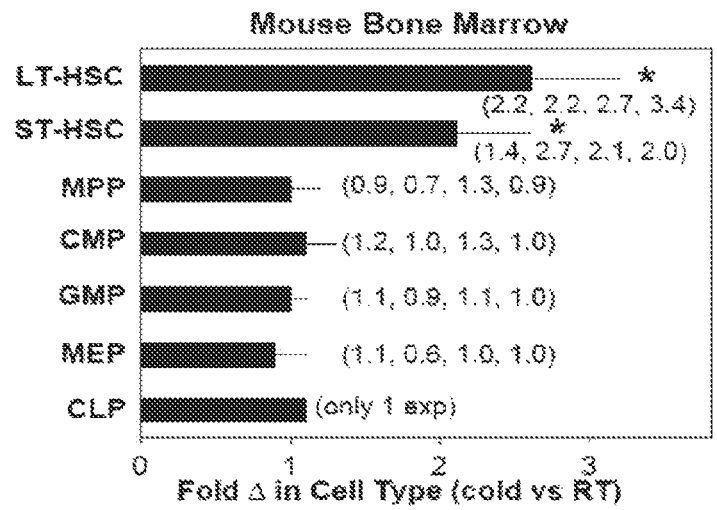
FIG. 1A. Graph illustrating the effects of different temperatures on the level of indicated cells from mouse bone marrow. The effects are measured in fold changes; the number of each cell type collected at 4° C. was compared to the number of each cell type collected at RT (room temperature). Results are shown as mean±SEM fold change of absolute numbers for 4 experiments (except for CLP; 1 experiment only) with the individual changes for each experiment shown in parentheses (* $p<0.001$ compared to RT collection and processing).

As used herein, unless explicitly stated otherwise or clearly implied otherwise the term 'about' refers to a range of values plus or minus 10 percent, e.g. about 1.0 encompasses values from 0.9 to 1.1.

The term, "treating" as used herein unless stated or implied otherwise, includes administering to a human or an animal patient at least one therapeutically effective dose of any of the compositions disclosed herein, treating includes lessening the severity of at least one disease as well as limiting the length of an illness or the severity of an illness, treating may or may not result in a cure of the disease. In one embodiment, treating includes preventing or lessening the likelihood of contracting a disease or illness.

As used herein, unless explicitly stated otherwise or clearly implied otherwise the terms 'therapeutically effective dose,' 'therapeutically effective amounts,' and the like, refer to an amount of one or more of the disclosed compositions that has/have a net positive effect on health and well being of a human or other animal. Therapeutic effects may include an improvement in longevity, quality of life and the like, as well as a reduced susceptibility to developing disease or deteriorating health or well being. The effects may be immediate, realized after a single dose and/or treatment, or they may be cumulative realized after a series of doses and/or treatments. A "therapeutically effective amount" in general means the amount that, when administered to a subject or animal for treating a disease, is sufficient to affect the desired degree of treatment for the disease.

As used herein, "inhibition" or "inhibitory activity" each encompass whole or partial reduction of activity or effect of an enzyme, or all and/or part of a pathway that includes an enzyme, that is effected either directly or indirectly by the inhibitor, or a pathway that is effected either directly or indirectly by the activity of the enzyme which is effected either directly or indirectly by the inhibitor.

As used herein, "clinical conditions," "illness" "diseases" and similar terms include, but are not limited to, conditions and/or diseases associated with insufficient quantity and/or quality of hematopoietic stem cells (HSCs). In certain embodiments, "clinical conditions" and/or "diseases" can include, but are not limited to, blood cancers (malignant and/or non-malignant), autoimmune diseases, hereditary skeletal dysplasias, and/or any other conditions associated with, induced by, or are already resistant to radiation or chemotherapy. Malignant cancers can include, but are not limited to, acute myeloid leukemia (AML), chronic myeloid leukemia (CIVIL), acute lymphoblastic leukemia (ALL), Hodgkin lymphoma (HL) (relapsed, refractory), Non-Hodgkin lymphoma (NHL) (relapsed, refractory), Neuroblastoma, Ewing sarcoma, multiple myeloma, myelodysplastic syndromes, gliomas, and other solid tumors. Non-malignant cancers can include, but are not limited to, thalassemia, sickle cell anemia, aplastic anemia, Fanconi anemia, malignant infantile osteopetrosis, mucopolysaccharidosis, immune deficiency syndromes, and autoimmune diseases. In some embodiments, the subject in need of hematopoietic reconstitution and/or diagnosed with conditions/diseases associated with insufficient quantity and/or quality of hematopoietic stem cells (HSCs) can have one or more of: a failure or dysfunction of normal blood cell production and maturation, anemia, a hematopoietic malignancy (e.g., leukemia, lymphoma), an autoimmune disease, a genetic disorder, an immunodeficiency (e.g., from irradiation, chemotherapy, infection) or any condition requiring a hematopoietic stem cell transplantation (HCT) procedure that is currently treated by cord blood, bone marrow or mobilized peripheral blood.

As used herein, "processing" unless explicitly stated otherwise or clearly implied otherwise refers to any maneuvers or manipulation of the cells including, but are not limited to, removal or isolation of cells, enrichment of selected cells, or purification/isolation of cells prior to freezing or cryopreservation.

As used herein, "cold" or "chilled" refers to about 1.5-5° C., preferably about 4° C. Unless explicitly stated otherwise or clearly implied otherwise, the terms, "cold" or "chilled" can be used interchangeably.

As used herein, "hematopoietic stem cells" or "HSCs" refer to multipotent stem cells that, under suitable conditions, can self-renew or differentiate into any blood cell type (e.g., a progenitor, intermediate or mature form of a lymphoid, myeloid, or platelet cell lineage). Myeloid cells can include, but are not limited to, monocytes, macrophages, neutrophils, basophils, eosinophils, erythrocytes, and megakaryocytes to platelets. Lymphoid cells can include, but are not limited to, T cells, B cells, and natural killer cells. HSCs are found, for example, in the bone marrow of adults, particularly in the pelvis, femur, and sternum. They are also found in umbilical cord blood and in peripheral blood. HSCs can be isolated from bone marrow, peripheral blood, umbilical cord blood, or pluripotent stem cells.

As used herein, "hematopoietic progenitor cells" or "HPCs" refer to precursor cells that are derived from differentiation of HSCs and are the immediate precursors of mature and/or differentiated hematopoietic cells. HPCs as used herein include, but are not limited to, colony forming cell/colony forming unit, granulocyte-macrophage-erythroid-megakaryocyte (CFC-GEMM; multipotential progenitors) colony-forming cells, granulocyte-macrophage colony-forming cells (GM-CFC), granulocyte colony forming cells (G-CFC), colony-forming cell-basophils (CFC-BAS), colony-forming cell-eosinophils (CFC-EO), macrophage colony-forming cells (M-CFC), macrophage colony-forming cells (CFU-M), megakaryocyte colony-forming cells (MK-CFC), burst-forming unit erythroid cells (BFU-E), B cell colony-forming cells (B-CFC), T cell colony-forming cells (T-CFC), and/or colony-forming unit-erythroid cells (CFU-E).

As used herein, "antioxidant" refers to an agent that inhibits the oxidation of other molecules. Oxidation is a chemical reaction that can produce free radicals. These free radicals are capable of attacking the healthy cells of the body. This may lead to damage, disease and severe disorders. Antioxidants can include, but are not limited to, thiols, vitamins (A, C, and/or E), uric acids, melatonin, glutathione, n-acetyl-cysteine (NAC), and/or ascorbic acid 2-phosphate (AAP).

As used herein, "epigenetic inhibitor" refers to an agent that alters gene expression and/or activity, but that does not alter the underlying nucleotide sequence itself. Examples of epigenetic inhibitors include, but are not limited to, agents that inhibit DNA methylation and agents that inhibit histone deacetylation. These agents include, but are not limited to, inhibitors of DNA methyltransferase, inhibitors of histone deacetylase, inhibitors of Aurora kinase, and/or inhibitors of poly [ADP-ribose] polymerase 1/2 (PARP1/2). In various embodiments, the epigenetic inhibitor can be an agent provided in Table 1.

TABLE 1

Exemplary Epigenetic Inhibitors

| Catalog # | CAS NUMBER | CHEMICAL NAME |
|---|---|---|
| S1451 | 1158838-45-9 | N-(2-Chlorophenyl)-4-(2-(4-(2-(4-ethylpiperazin-1-yl)-2-oxoethyl)phenylamino)-5-fluoro-pyrimidin-4-ylamino)benzamide, N-(2-Chlorophenyl)-4-[[2-[[4-[2-(4-ethyl-1-piperazinyl)-2-oxoethyl]phen-yl]amino]-5-fluoro-4-pyrimidinyl]amino]-benzamide |
| S1103 | 331771-20-1 | 4-(4-(N-Benzoylamino)anilino)-6-methoxy-7-(3-(1-morpholino)propoxy)quinazoline (ZM447439) |
| S1147 | 722544-51-6 | 3-[[7-[3-[Ethyl(2-hydroxyethyl)amino]propoxy]-4-quinazolinyl]amino]-N-(3-fluoro-phenyl)-1H-pyrazole-5-acetamide (AZD1152) |
| S2821 | 48208-26-0 | N-Phthalyl-L-tryptophan (RG108) |
| S1200 | 2353-33-5 | 5-Aza-2'-deoxycytidine |
| S1782 | 320-67-2 | AZACITIDINE |
| S1060 | 763113-22-0 | OLAPARIB |
| S1004 | 912444-00-9 | VELIPARIB |
| S2886 | 344458-15-7 | PJ34 HCL |

As used herein, "ambient air" or "ambient air condition" refers to atmospheric air in its natural state. Ambient air is typically about 78% nitrogen and about 21% oxygen. Preferably, the oxygen tension of ambient air is about 20%.

As used herein, "hypoxia," "hypoxic air" or "hypoxic condition" refers to air comprising an oxygen tension of less than 10%, 9%, 8%, 7%, 6%, 5%, 4%, 3%, 2%, and/or 1%. Preferably, the oxygen tension of hypoxic air is about 3%.

Pharmaceutical formulations of the present disclosure suitable for oral administration can be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation can also be a bolus, electuary or paste.

Pharmaceutical formulations of the present disclosure suitable for parenteral administration include aqueous and non-aqueous sterile injection solutions, and can also include an antioxidant, buffer, a bacteriostat and a solution which renders the composition isotonic with the blood of the recipient, and aqueous and non-aqueous sterile suspensions which can contain, for example, a suspending agent and a thickening agent. The formulations can be presented in a single unit-dose or multi-dose containers, and can be stored in a lyophilized condition requiring the addition of a sterile liquid carrier prior to use.

"Pharmaceutically acceptable carrier," unless stated or implied otherwise, is used herein to describe any ingredient other than the active component(s) that can be included in a formulation. The choice of carrier will to a large extent depend on factors such as the particular mode of administration, the effect of the carrier on solubility and stability, and the nature of the dosage form.

A tablet can be made by compressing or moulding the active ingredient with the pharmaceutically acceptable carrier. Compressed tablets can be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets can be prepared by moulding in a suitable machine a mixture of the powdered active ingredient moistened with an inert liquid diluent. The tablets can optionally be coated or scored and can be formulated so as to provide slow or controlled release of the active ingredient.

The term, "synergism" or "synergy" refers to an interaction of two or more factors such that the effect when combined is greater than the predicted effect based on the response of each factor applied separately.

DETAILED DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Hematopoietic stem cells (HSCs) reside in a hypoxic microenvironment in vivo (about 1-5% $O_2$). Contact with ambient air (about 20-21% $O_2$) can induce HSCs to differentiate into hematopoietic progenitor cells (HPCs). Most studies and hematopoietic cell transplantation (HCT) are carried out in ambient air, and therefore, these experiments are exposed to the problem known as extraphysiologic oxygen shock/stress (EPHOSS). Collection of cells under hypoxic conditions, for example in a hypoxia chamber (at 3% $O_2$), can greatly increase HSC recovery from mouse bone marrow (BM) and human cord blood (CB). Further, the effects of EPHOSS can be reversed in part if the collections are performed in presence of cyclosporine A. However, due in part to the limited availability of hypoxia chambers at the collection center and the cellular toxicity of cyclosporine A, these procedures provide certain limitations. Therefore, a new development of processes/methods that could overcome the effects of EPHOSS is much needed.

Umbilical cord blood transplantation has been used to treat malignant and non-malignant disorders in over 40,000 patients, many of whom had no other treatment alternatives. The origins of the field of umbilical cord blood (cord blood) hematopoietic cell transplantation (HCT) have been previously studied. The use of cord blood rather than bone marrow or mobilized peripheral blood for transplantation may be advantageous due in part to the availability of cord blood units and/or to the lower incidents of acute graft versus host disease in patients.

Umbilical cord blood is typically collected via a needle or cannula under ambient air conditions (e.g., about 20% $O_2$), which is used to drain cord blood from the placenta with the aid of gravity into a collection vessel (e.g., a sterile bag(s) or vial(s)). Typically, shortly after delivery, the umbilical cord is clamped, the baby is separated from the cord, a cannula is inserted into the vein of the umbilical cord and then the blood is drawn from the umbilical cord and placenta, through the cannula, into one or more sterile collection bags or vessels, which usually contains an anti-coagulant compound or composition for receiving the collected blood (e.g., EDTA and/or heparin). The collection vessel(s) may then be placed in a container for transport and/or shipment to a facility where the collected cord blood can be processed and prepared for storage after freezing (cryopreservation).

One consideration for collecting cord blood suitable for subsequent HCT is sterility. Accordingly, kits for collection of cord blood (see below) typically include reagents and/or instructions for cleaning the surface of the umbilical cord where the cannula will be inserted and sterile devices for collecting and containing the collected cord blood. Further, processing of the collected cord blood may involve testing of the cord blood for microbial and viral contamination, as well as a number of other parameters such as human leukocyte antigen (HLA) histocompatibility testing.

Another consideration for collecting cord blood suitable for subsequent HCT is temperature. Traditionally, cord blood cells (e.g., stem cells) were thought to not tolerate sharp or sustained deviations from a temperature range of about room temperature (e.g., about 21° C.) to body temperature (e.g., 37° C.) (see, e.g., U.S. Pat. No. 7,909,806). For this reason, cord blood collection kits and service providers have traditionally recommended collecting and maintaining cord blood samples at room temperature or between 15-37° C.

Recently, the American College of Obstetricians and Gynecologists released a position statement on delayed cord blood clamping that recommended an interval of 30-60 seconds after delivery of healthy term babies, which means that a lesser volume of cord blood will be collected, which in turn means that fewer HSCs will be present in the collected cord blood units. As noted above, HSCs are the cells that give rise to HPCs and all the blood forming elements (e.g., white blood cells, red blood cells, platelets) and are required for life-long production of all the blood cells. Thus, it is imperative that there be enough of these cells in the collections to ensure the adequate replacement of the blood cells that have limited life-spans.

One method for enhancing the collection of HSCs from cord blood, even if clamping is delayed, is to perfuse the cord blood and placenta with saline or other suitable liquid after delivery, which results in the collection of greater volumes of cord blood with increased numbers of HSCs and HPCs. However, this procedure is very cumbersome and time-consuming and has not found widespread use in collection centers, or been used for units stored in unrelated (public) or family (private) cord blood banks.

Another method that has resulted in the collection of 2-5 fold more HSCs/cord blood unit is collection and processing of cord blood cells under hypoxic (e.g., 3% $O_2$) conditions. Hypoxic collection/processing of the cells prevents loss of HSCs induced by contact with ambient air and an associated phenomenon termed extra physiological oxygen shock/stress (EPHOSS) which causes rapid differentiation of a large proportion of HSCs in the cord blood upon short-term exposure to ambient air. Thus, untreated cord blood collected and processed in ambient air has fewer HSCs and more HPCs than cells collected and processed in hypoxic (e.g., 3% $O_2$) conditions. In contrast, cord blood collected/processed in 3% $O_2$ has more HSCs, but fewer HPCs. While countering EPHOSS by the hypoxic collection/processing could obviate problems of limited HSC numbers in single cord blood collections, it is not a procedure that lends itself to routine use at cord blood collection centers.

An alternative method for blocking EPHOSS-induced differentiation and enhanced HSC collection is collection and processing of cord blood in ambient air and in the continued presence of cyclosporine A. This procedure has not currently been implemented at cord blood collection centers and would require further optimization and experimentation to be implemented because batches of cyclosporine A are not always equivalent in potency, the cyclosporine A has to be titrated to determine optimal effectiveness, and exposure of the collected cells for prolonged periods can be toxic to the cells.

Embodiments of the instant application relate to compositions and to methods for collecting and processing bone marrow, umbilical cord blood, and/or peripheral blood of a subject. In certain embodiments, compositions and methods disclosed herein concern enrichment of hematopoietic stem cells and their use in transplantation. Other embodiments relate to compositions and methods for treating a subject diagnosed with a disease or having a condition contributed to cancers, autoimmune diseases, hereditary skeletal dysplasias, infections, graft-versus-host diseases, and/or any other conditions associated with, induced by, or are already resistant to radiation or chemotherapy.

Compositions

In some embodiments, compositions disclosed herein include: a portion of bone marrow, umbilical cord blood, and/or peripheral blood of a subject; a first antioxidant; and a second antioxidant. Consistent with this embodiment, the first antioxidant and the second antioxidant are independently selected from thiols, vitamin A, vitamin C, vitamin E, uric acids, melatonin, glutathione, n-acetyl-cysteine (NAC), and/or ascorbic acid 2-phosphate (AAP). In certain embodiments, the first antioxidant can be n-acetyl-cysteine (NAC) and the second antioxidant can be selected from thiols, vitamin A, vitamin C, vitamin E, uric acids, melatonin, glutathione, and/or ascorbic acid 2-phosphate (AAP). In other embodiments, the first antioxidant is n-acetyl-cysteine (NAC) and the second antioxidant is ascorbic acid 2-phosphate (AAP). In accordance with these embodiments, the compositions can be placed and/or maintained in ambient air (comprising from about 20% to about 21% $O_2$) or in hypoxia (comprising from about 2.5% to about 3.5% $O_2$); and/or the composition can be placed and/or maintained at a temperature from about 1° C. to about 5° C. or from about 18° C. to about 24° C.

Consistent with these embodiments, the first antioxidant and the second antioxidant are present in the composition in a concentration ratio such that the composition exhibits synergy. The concentration ratio of the first antioxidant and the second antioxidant can be from about 10:1 to about 1:10, from about 9:1 to about 1:9, from about 8:1 to 1:8, from about 5:1 to about 1:5, from about 2:1 to about 1:2, about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or any combination(s) thereof.

In some embodiments, the compositions can further include at least one agent that alters gene expression. The at least one agent that alters gene expression can include, but is not limited to, a DNA methyltransferase inhibitor, an Aurora kinase inhibitor, a PARP1/2 inhibitor, or any combination thereof. The at least one agent that alters gene expression can include, but is not limited to, N-(2-Chlorophenyl)-4-(2-(4-(2-(4-ethylpiperazin-1-yl)-2-oxoethyl)phenylamino)-5-fluoropyrimidin-4-ylamino)benzamide, N-(2-Chlorophenyl)-4-[[2-[[4-[2-(4-ethyl-1-piperazinyl)-2-oxoethyl]phenyl]amino]-5-fluoro-4-pyrimidinyl]amino]-benzamide, 4-(4-(N-Benzoylamino)anilino)-6-methoxy-7-(3-(1-morpholino)propoxy)quinazoline, 3-[[7-[3-[Ethyl(2-hydroxyethyl)amino]propoxy]-4-quinazolinyl]amino]-N-(3-fluorophenyl)-1H-pyrazole-5-acetamide, N-Phthalyl-L-tryptopha, 5-Aza-2'-deoxycytidine, azacitidine, olaparib, veliparib, PJ34 HCL, or any combination thereof.

Other embodiments include the first antioxidant having a concentration from about 0.01 mM to about 5 mM, from about 0.05 mM to about 3 mM, from about 0.1 mM to about 2 mM, from about 0.2 mM to about 1 mM, from about 0.5 mM to about 1 mM, from about 0.8 mM to about 1 mM, about 0.5 mM, about 1 mM, about 1.5 mM, about 2 mM, about 2.5 mM, about 3 mM, or any combinations thereof. Consistent with these embodiments, some embodiments include the second antioxidant having a concentration from about 0.01 mM to about 5 mM, from about 0.05 mM to about 3 mM, from about 0.1 mM to about 2 mM, from about 0.2 mM to about 1 mM, about 0.1 mM, about 0.15 mM, about 0.16 mM, about 0.17 mM, about 0.18 mM, about 0.19 mM, about 0.2 mM, about 0.21 mM, about 0.22 mM, about 0.23 mM, about 0.24 mM, about 0.25 mM, about 0.3 mM, or any combinations thereof.

In accordance with these embodiments, the composition is placed and/or maintained in ambient air comprising from about 18% $O_2$ to about 23% $O_2$, from about 19% $O_2$ to about 22% $O_2$, from about 20% $O_2$ to about 22% $O_2$, from about 20% $O_2$ to about 21% $O_2$, about 18% $O_2$, about 19% $O_2$, about 20% $O_2$, about 21% $O_2$, about 22% $O_2$, about 23% $O_2$, or any combinations thereof. In other embodiments, the composition is placed and/or maintained in hypoxia comprising from about 1% $O_2$ to about 5% $O_2$, from about 2% $O_2$ to about 4% $O_2$, from about 2% $O_2$ to about 3% $O_2$, about 1% $O_2$, about 2% $O_2$, about 3% $O_2$, about 4% $O_2$, about 5% $O_2$, or any combinations thereof. Yet in other embodiments, the composition is placed and/or maintained at a temperature from about 1° C. to about 5° C., from about 2° C. to about 4° C., from about 3° C. to about 4° C., about 1° C., about 2° C., about 3° C., about 4° C., about 5° C., or any combination thereof; and/or the composition is placed and/or maintained at a temperature from about 16° C. to about 25° C., from about 18° C. to about 23° C., from about 20° C. to about 22° C., about 18° C., about 19° C., about 20° C., about 21° C., about 22° C., or any combination thereof.

In accordance with any of the embodiments disclosed herein, the portion of bone marrow, umbilical cord blood, and/or peripheral blood includes hematopoietic stem cells; and the subject includes, but is not limited to, a human or an animal. In any one of embodiments disclosed herein, the portion of bone marrow, umbilical cord blood, and/or peripheral blood comprises hematopoietic stem cells, and the composition comprises hematopoietic stem cells.

In certain embodiments, compositions disclosed herein include a portion of bone marrow, umbilical cord blood, and/or peripheral blood of a subject; and at least one agent that alters gene expression. Consistent with this embodiment, the agent that alters gene expression comprises at least one inhibitor of DNA methylation and/or histone deacetylation; and can include, but is not limited to, a DNA methyltransferase inhibitor, an Aurora kinase inhibitor, a PARP1/2 inhibitor, or any combination thereof. In accordance with these embodiments, the compositions can be placed and/or maintained in ambient air (comprising from about 20% to about 21% $O_2$) or in hypoxia (comprising from about 2.5% to about 3.5% $O_2$); and/or the composition can be placed and/or maintained at a temperature from about 1° C. to about 5° C. or from about 18° C. to about 24° C.

Consistent with these embodiments, the at least one agent that alters gene expression can include, but is not limited to, N-(2-Chlorophenyl)-4-(2-(4-(2-(4-ethylpiperazin-1-yl)-2-oxoethyl)phenylamino)-5-fluoropyrimidin-4-ylamino)benzamide, N-(2-Chlorophenyl)-4-[[2-[[4-[2-(4-ethyl-1-piperazinyl)-2-oxoethyl]phenyl]amino]-5-fluoro-4-pyrimidinyl]amino]-benzamide, 4-(4-(N-Benzoylamino)anilino)-6-methoxy-7-(3-(1-morpholino)propoxy)quinazoline, 3-[[7-[3-[Ethyl(2-hydroxyethyl)amino]propoxy]-4-quinazolinyl]amino]-N-(3-fluorophenyl)-1H-pyrazole-5-acetamide, N-Phthalyl-L-tryptopha, 5-Aza-2'-deoxycytidine, azacitidine, olaparib, veliparib, PJ34 HCL, or any combination thereof. Certain embodiments include the at least one agent that alters gene expression having a concentration of from about 1 µM to about 100 µM, from about 1 µM to about 20 µM, from about 1 µM to about 15 µM, from about 1 µM to about 10 µM, from about 1 µM to about 5 µM, from about 5 µM to about 20 µM, from about 5 µM to about 15 µM, from about 5 µM to about 12 µM, from about 8 µM to about 10 µM, about 1 µM, about 2 µM, about 3 µM, about 4 µM, about 5 µM, about 6 µM, about 7 µM, about 8 µM, about 9 µM, about 10 µM, about 11 µM, about 12 µM, about 13 µM, about 14 µM, about 15 µM, or any combinations thereof In accordance with these embodiments, the composition is placed and/or maintained in ambient air comprising from about 18% $O_2$ to about 23% $O_2$, from about 19% $O_2$ to about 22% $O_2$, from about 20% $O_2$ to about 22% $O_2$, from about 20% $O_2$ to about 21% $O_2$, about 18% $O_2$, about 19% $O_2$, about 20% $O_2$, about 21% $O_2$, about 22% $O_2$, about 23% $O_2$, or any combinations thereof. In other embodiments, the composition is placed and/or maintained in hypoxia comprising from about 1% $O_2$ to about 5% $O_2$, from about 2% $O_2$ to about 4% $O_2$, from about 2% $O_2$ to about 3% $O_2$, about 1% $O_2$, about 2% $O_2$, about 3% $O_2$, about 4% $O_2$, about 5% $O_2$, or any combinations thereof. Yet in other embodiments, the composition is placed and/or maintained at a temperature from about 1° C. to about 5° C., from about 2° C. to about 4° C., from about 3° C. to about 4° C., about 1° C., about 2° C., about 3° C., about 4° C., about 5° C., or any combination thereof; and/or the composition is placed and/or maintained at a temperature from about 16° C. to about 25° C., from about 18° C. to about 23° C., from about 20° C. to about 22° C., about 18° C., about 19° C., about 20° C., about 21° C., about 22° C., or any combination thereof.

Yet in other embodiments, compositions disclosed herein include a first antioxidant; and a second antioxidant, wherein the composition is added to a portion of bone marrow, umbilical cord blood, and/or peripheral blood of a subject. Consistent with this embodiment, the first antioxidant and the second antioxidant are independently selected from thiols, vitamin A, vitamin C, vitamin E, uric acids, melatonin, glutathione, n-acetyl-cysteine (NAC), and/or ascorbic acid 2-phosphate (AAP). In certain embodiments, the first antioxidant can be n-acetyl-cysteine (NAC) and the second antioxidant can be selected from thiols, vitamin A, vitamin C, vitamin E, uric acids, melatonin, glutathione, and/or ascorbic acid 2-phosphate (AAP). In other embodiments, the first antioxidant is n-acetyl-cysteine (NAC) and the second antioxidant is ascorbic acid 2-phosphate (AAP). In accordance with these embodiments, the compositions can be placed and/or maintained in ambient air (comprising from about 20% to about 21% $O_2$) or in hypoxia (comprising from about 2.5% to about 3.5% $O_2$); and/or the composition can be placed and/or maintained at a temperature from about 1° C. to about 5° C. or from about 18° C. to about 24° C. In these embodiments, the compositions can further include at least one agent that alters gene expression. The at least one agent that alters gene expression can include, but are not limited to, a DNA methyltransferase inhibitor, an Aurora kinase inhibitor, a PARP1/2 inhibitor, or any combination thereof.

Consistent with these embodiments, the first antioxidant and the second antioxidant is present in the composition in a concentration ratio such that the composition exhibits synergy. The concentration ratio of the first antioxidant and the second antioxidant can be from about 10:1 to about 1:10, from about 9:1 to about 1:9, from about 8:1 to 1:8, from about 5:1 to about 1:5, from about 2:1 to about 1:2, about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or any combination(s) thereof.

In some embodiments, the compositions can further include at least one agent that alters gene expression. The at least one agent that alters gene expression can include, but is not limited to, a DNA methyltransferase inhibitor, an Aurora kinase inhibitor, a PARP1/2 inhibitor, or any combination thereof. The at least one agent that alters gene expression can include, but is not limited to, N-(2-Chlorophenyl)-4-(2-(4-(2-(4-ethylpiperazin-1-yl)-2-oxoethyl)phenylamino)-5-fluoropyrimidin-4-ylamino)benzamide, N-(2-Chlorophenyl)-4-[[2-[[4-[2-(4-ethyl-1-piperazinyl)-2-oxoethyl]phenyl]amino]-5-fluoro-4-pyrimidinyl]amino]-benzamide, 4-(4-(N-Benzoylamino)anilino)-6-methoxy-7-(3-(1-morpholino)propoxy)quinazoline, 3-[[7-[3-[Ethyl(2-hydroxyethyl)amino]propoxy]-4-quinazolinyl]amino]-N-(3-fluorophenyl)-1H-pyrazole-5-acetamide, N-Phthalyl-L-tryptopha, 5-Aza-2'-deoxycytidine, azacitidine, olaparib, veliparib, PJ34 HCL, or any combination thereof.

Other embodiments includes the first antioxidant having a concentration from about 0.01 mM to about 5 mM, from about 0.05 mM to about 3 mM, from about 0.1 mM to about 2 mM, from about 0.2 mM to about 1 mM, from about 0.5 mM to about 1 mM, from about 0.8 mM to about 1 mM, about 0.5 mM, about 1 mM, about 1.5 mM, about 2 mM, about 2.5 mM, about 3 mM, or any combinations thereof. Consistent with these embodiments, some embodiments includes the second antioxidant having a concentration from about 0.01 mM to about 5 mM, from about 0.05 mM to about 3 mM, from about 0.1 mM to about 2 mM, from about 0.2 mM to about 1 mM, about 0.1 mM, about 0.15 mM, about 0.16 mM, about 0.17 mM, about 0.18 mM, about 0.19 mM, about 0.2 mM, about 0.21 mM, about 0.22 mM, about 0.23 mM, about 0.24 mM, about 0.25 mM, about 0.3 mM, or any combinations thereof.

In accordance with these embodiments, the composition is placed and/or maintained in ambient air comprising from about 18% $O_2$ to about 23% $O_2$, from about 19% $O_2$ to about 22% $O_2$, from about 20% $O_2$ to about 22% $O_2$, from about 20% $O_2$ to about 21% $O_2$, about 18% $O_2$, about 19% $O_2$, about 20% $O_2$, about 21% $O_2$, about 22% $O_2$, about 23% $O_2$, or any combinations thereof. In other embodiments, the composition is placed and/or maintained in hypoxia comprising from about 1% $O_2$ to about 5% $O_2$, from about 2% $O_2$ to about 4% $O_2$, from about 2% $O_2$ to about 3% $O_2$, about 1% $O_2$, about 2% $O_2$, about 3% $O_2$, about 4% $O_2$, about 5% $O_2$, or any combinations thereof. Yet in other embodiments, the composition is placed and/or maintained at a temperature from about 1° C. to about 5° C., from about 2° C. to about 4° C., from about 3° C. to about 4° C., about 1° C., about 2° C., about 3° C., about 4° C., about 5° C., or any combination thereof; and/or the composition is placed and/or maintained at a temperature from about 16° C. to about 25° C., from about 18° C. to about 23° C., from about 20° C. to about 22° C., about 18° C., about 19° C., about 20° C., about 21° C., about 22° C., or any combination thereof.

In some embodiments, methods disclosed herein include a method of treating a clinical condition, comprising the step of: providing a subject at least one therapeutically effective dose of any of compositions disclosed herein. The subject can be diagnosed with a clinical condition selected from and/or comprising cancers, autoimmune diseases, hereditary skeletal dysplasias, infections, graft-versus-host diseases, and/or any other conditions associated with, induced by, or are already resistant to radiation or chemotherapy. Consistent with these embodiments, the subject is diagnosed with a clinical condition comprising acute myeloid leukemia (AML), chronic myeloid leukemia (CIVIL), acute lymphoblastic leukemia (ALL), Hodgkin lymphoma (HL) (relapsed, refractory), Non-Hodgkin lymphoma (NHL) (relapsed, refractory), neuroblastoma, Ewing sarcoma, multiple myeloma, myelodysplastic syndromes, gliomas, solid tumors, thalassemia, sickle cell anemia, aplastic anemia, Fanconi anemia, malignant infantile osteopetrosis, mucopolysaccharidosis, immune deficiency syndromes, infections, graft-versus-host diseases, and/or autoimmune diseases. Further, the methods disclosed herein includes further step of providing the subject at least one additional therapeutically effective dose of any one of compositions disclosed herein; and the composition comprises hematopoietic stem cells that are autologous, allogeneic, or syngeneic, or any combination thereof. In accordance with these embodiments, the methods can include the step of removing the first antioxidant, the second antioxidant, and/or the at least one agent that alters gene expression from the composition.

Yet other embodiments can include methods for collecting bone marrow, cord blood, and/or peripheral blood of a subject in ambient air (comprising from about 20% to about 21% $O_2$) at a temperature from about 1° C. to about 5° C. Consistent with these embodiments, the methods further include the step of isolating hematopoietic stem cells (HSCs). In certain embodiments, the bone marrow, cord blood, and/or peripheral blood can be placed and/or maintained in ambient air (comprising from about 20% to about 21% $O_2$) and at a temperature from about 3° C. to about 5°

C. In accordance with these embodiments, the isolated populations of HSCs can include CD34$^+$CD38$^-$ HSCs. The subject in accordance with these embodiments can include humans and animals.

In accordance with these embodiments, the bone marrow, cord blood, and/or peripheral blood of a subject is placed and/or maintained in ambient air comprising from about 18% $O_2$ to about 23% $O_2$, from about 19% $O_2$ to about 22% $O_2$, from about 20% $O_2$ to about 22% $O_2$, from about 20% $O_2$ to about 21% $O_2$, about 18% $O_2$, about 19% $O_2$, about 20% $O_2$, about 21% $O_2$, about 22% $O_2$, about 23% $O_2$, or any combinations thereof. In other embodiments, the bone marrow, cord blood, and/or peripheral blood of a subject is placed and/or maintained in hypoxia comprising from about 1% $O_2$ to about 5% $O_2$, from about 2% $O_2$ to about 4% $O_2$, from about 2% $O_2$ to about 3% $O_2$, about 1% $O_2$, about 2% $O_2$, about 3% $O_2$, about 4% $O_2$, about 5% $O_2$, or any combinations thereof. Yet in other embodiments, the bone marrow, cord blood, and/or peripheral blood of a subject is placed and/or maintained at a temperature from about 1° C. to about 5° C., from about 2° C. to about 4° C., from about 3° C. to about 4° C., about 1° C., about 2° C., about 3° C., about 4° C., about 5° C., or any combination thereof; and/or is placed and/or maintained at a temperature from about 16° C. to about 25° C., from about 18° C. to about 23° C., from about 20° C. to about 22° C., about 18° C., about 19° C., about 20° C., about 21° C., about 22° C., or any combination thereof.

Generally, the present disclosure provides a method for enhanced collection of cord blood having an increased number of HSCs relative to cord blood collected using standard protocols. An aspect of the present disclosure is based on the surprising discovery that collecting and processing human cord blood units in ambient air (i.e., having an oxygen tension of about 20%) and under cold temperatures, rather than at room temperature, increases the number of HSCs retained in the collected cord blood. The method can be carried out at room temperature as long as the vessel the cord blood is going into is chilled to about 4° C. (e.g., the collection must be immediately into a cold collection vessel, but the room can be room temperature).

An aspect of the present disclosure includes collecting and/or processing human cord blood units in ambient air in the presence of at least two antioxidants. Such collecting and/or processing increases the number of HSCs retained in the collected cord blood. Certain aspect of the present disclosure includes collecting and/or processing human cord blood units in ambient air in the presence of one or more epigenetic inhibitors, which increases the number of HSCs retained in the collected cord blood.

Methods of Collecting and Processing Bone Marrow, Peripheral Blood and/or Cord Blood from Umbilical Cord and/or Placenta In the present disclosure, it is shown that the collection and processing of mouse bone marrow cells in ambient air in the presence of specific combinations of antioxidants and/or inhibitors of epigenetic enzymes can enhance the collection of HSC, thus leading to the enhanced efficacy of HCT.

In the present disclosure, new methods of collecting/recovering HSCs from a portion of bone marrow, umbilical cord blood, and/or peripheral blood of a subject are disclosed. By utilizing one or more combinations of the methods and/or compounds disclosed herein, the effects of 'hypoxia harvest' on HSCs can be mimicked. Certain combinations of antioxidants and/or epigenetic enzyme inhibitors could further enhance the collection of HSCs not only in ambient air but also in hypoxia, for example under conditions having about 3% $O_2$. While the following disclosure relates to cord blood, a person skilled in the art will recognize that the methods will also be readily applicable to the collection and processing of bone marrow and/or peripheral blood.

In an aspect, a method for collecting cord blood is provided. The method includes collecting cord blood from an umbilical cord in a collection medium (e.g., containing anti-coagulants) that is chilled (e.g., in one embodiment at about 4° C.). The blood is drawn into a chilled environment. Any transport of the drawn cord blood also occurs with the blood in a chilled environment.

In some embodiments, cord blood collected using the method provided herein comprises an increased number of HSCs relative to a similar volume of cord blood collected under room temperature conditions. This is a surprising and significant change in current cord blood collection and processing procedures at least because many current procedures specify that cord blood collection and transport prior to processing should be carried out at room temperature or between room temperature and body temperature. Indeed, some instructions for collection of cord blood explicitly disclose that cord blood should not be refrigerated, because refrigeration may damage the collected cells (see, e.g., Umbilical Cord Blood Collection Training presentation by the Cord Blood Bank of Arkansas).

In certain embodiments, the cord blood is collected immediately into chilled media, for example, by being drawn into the chilled media. This method results in collected cord blood that comprises an increased number of HSCs relative to a similar volume of cord blood collected under room temperature conditions. This is surprising at least because ambient air is known to induced loss of HSCs through extraphysiologic oxygen shock/stress (EPHOSS), which causes rapid differentiation of a large proportion of HSCs in the cord blood upon short-term exposure to ambient air, resulting in collected cord blood with relatively few HSCs and relatively more HPCs. Without being bound by theory, it is contemplated herein that the increased number of HSCs in the cord blood units collected using the method provided herein is due, at least in part, to a decrease in differentiation of HSCs to HPCs.

In accordance with these embodiments, the method provided herein further involves maintaining the chilled collected cord blood in a chilled environment/at a cold temperature (e.g., about 4° C.) during any processing of the cells and transport of the cells prior to their freezing for cryopreservation. For example, after collection and immediate chilling to a cold temperature, the chilled collected sample is maintained at the cold temperature during transport to a cord blood processing facility. In an embodiment, the method provided herein further involves processing the chilled collected cord blood at a cold temperature (e.g., in one embodiment at about 4° C.).

In other embodiments, the method may be used to generate a population of cord blood-derived HSCs having more HSCs relative to a population of cord blood-derived HSCs generated from cord blood collected and/or processed at room temperature. In an embodiment, the method may be used to generate a population of cord blood-derived HSCs having fewer HPCs relative to a population of cord blood-derived HSCs generated from cord blood collected and/or processed at room temperature.

In another aspect, a method for collecting cord blood is provided. The method includes collecting cord blood from an umbilical cord in the presence of two or more antioxidants. In an embodiment, the antioxidants are N-Acetylcysteine and ascorbic acid 2-phosphate. In another embodiment, the two or more antioxidants are independently selected from uric acid, melatonin, and Vitamin E. In another embodiment the collecting and/or processing occurs under ambient air conditions. In an embodiment, cord blood collected using the method provided herein comprises an increased number of HSCs relative to a similar volume of cord blood collected in the absence of the two or more antioxidants.

Without being bound by theory, it is contemplated herein that the increased number of HSCs in the cord blood units collected using the method provided herein is due to a decrease in differentiation of HSCs to HPCs. In an embodiment, the method may be used to generate a population of cord blood-derived HSCs having more HSCs relative to a population of cord blood-derived HSCs generated from cord blood collected and/or processed in the absence of the two or more antioxidants. In an embodiment, the method may be used to generate a population of cord blood-derived HSCs having fewer HPCs relative to a population of cord blood-derived HSCs generated from cord blood collected and/or processed in the absence of the two or more antioxidants.

In a further aspect, a method for collecting cord blood is provided. The method includes collecting cord blood from an umbilical cord in the presence at least one epigenetic inhibitor. In an embodiment, the epigenetic inhibitor is an inhibitor of Aurora kinase, an inhibitor of DNA methyltransferase or an inhibitor of PARP1/2. In an embodiment, the inhibitor of Aurora kinase is s1451, s1103 or s1147. In an embodiment the inhibitor of DNA methyltransferase is s2821, ss1200 or s1782. In an embodiment the inhibitor of PARP1/2 is s1060, s1004 or s2886. In a certain embodiment, the method occurs in the presence of an inhibitor of Aurora kinase and an inhibitor of DNA methyltransferase. It will be appreciated that the at least one epigenetic inhibitor is not limited to an inhibitor of a specific event and thus is not limited to the Aurora kinase, DNA methyltransferase or PARP1/2 inhibitors referenced above, but may include other compounds that alter gene expression and/or activity but that does not alter the underlying nucleotide sequence itself. In an embodiment, the method occurs in the presence of an inhibitor of Aurora kinase and an inhibitor of PARP1/2. In another embodiment, the collecting occurs under ambient air conditions. In another embodiment the collecting occurs under hypoxic (e.g., in one embodiment at about 3% $O_2$) conditions. In another embodiment, the collecting and/or processing occurs in a chilled air temperature (e.g., in one embodiment at about 4° C.). In an embodiment, cord blood collected using the method provided herein comprises an increased number of HSCs relative to a similar volume of cord blood collected in the absence of the at least one epigenetic inhibitor.

Without being bound by theory, it is contemplated herein that the increased number of HSCs in the cord blood units collected using the method provided herein is due to a decrease in differentiation of HSCs to HPCs. In an embodiment, the method may be used to generate a population of cord blood-derived HSCs having more HSCs relative to a population of cord blood-derived HSCs generated from cord blood collected and/or processed in the absence of the at least one epigenetic inhibitor. In an embodiment, the method may be used to generate a population of cord blood-derived HSCs having fewer HPCs relative to a population of cord blood-derived HSCs generated from cord blood collected and/or processed in the absence of the at least one epigenetic inhibitor.

Therapeutic Uses

Hematopoietic cell transplantation (HCT) is a treatment for malignant and nonmalignant disorders. However, sometimes the numbers of donor hematopoietic stem cells (HSC) are limiting, which can compromise the success of HCT. Recent studies provide that collection and processing of mouse bone marrow and human cord blood cells in a hypoxic atmosphere of 3% $O_2$ or in ambient air (about 21% $O_2$) in the presence of cyclosporine A yields increased numbers of HSC.

In an aspect, the population of cord-blood derived HSCs generated using the methods provided herein may be used to treat a subject in need of hematopoietic reconstitution. The intended purpose may be, for example, repopulation of the blood cell system after either full or partial myeloablation to prepare the recipient for the repopulating cells (e.g., HSCs). The amount of cord-blood derived HSCs generated using the methods provided herein and/or compositions provided by the present disclosure administered may vary from one subject to another and may depend upon one or more factors, such as, for example, subject gender, age, body weight, subject's health history, the underlying cause of the condition to be prevented, inhibited and/or treated, and the judgment of the administering health care professional. The term, "in need of hematopoietic reconstitution" can refer to a subject having a condition associated with insufficient quantity and/or quality of hematopoietic cells. In an embodiment, the subject in need of hematopoietic reconstitution has one or more of: a failure or dysfunction of normal blood cell production and maturation, anemia, a hematopoietic malignancy (e.g., leukemia, lymphoma), an autoimmune disease, a genetic disorder, an immunodeficiency (e.g., from irradiation, chemotherapy, infection) or any condition requiring a hematopoietic stem cell transplantation (HCT) procedure that is currently treated by cord blood, bone marrow or mobilized peripheral blood.

In an embodiment, the method comprises introducing into the subject a therapeutically effective amount of the cord-blood containing HSCs generated using one or more of the methods provided herein, whereby hematopoietic reconstitution is affected in the treated subject. The methods of treatment provided herein may be implemented using techniques for HCT known in the art. As a skilled person will appreciate, the methods provided herein may be used alone or in combination with other therapies/methods to further enhance cord blood HCT. For example, in an embodiment, the method comprises, prior to introduction of the cells into the subject, processing of the cord blood-derived HSCs. For example, the cells may be processed by one or more of enrichment procedures (i.e., ex-vivo expansion of the HSCs), and cryopreserving the cord-blood derived HSCs, prior to or after enhancing the capacity to more efficiently home to the bone marrow for more efficacious engraftment.

It is contemplated herein that the collected cord blood cells provided herein may be expanded ex vivo, for example using methods known in the art, such as treatment with cytokines and SR1, treatment with UM171 or other small molecule(s). However, it is also contemplated that ex-vivo expansion may not be needed if the collected cord blood contains enough HSCs to effect efficient hematopoietic reconstitution in a subject. Yet in other embodiments disclosed herein, it is contemplated that the collected cord blood cells provided herein may be pretreated ex-vivo to enhance their engraftment in a subject, such as, for example, by fucosylation, PGE, DPP4 inhibition, hyperthermia, glucocorticoid stimulation or combinations of any of the foregoing.

In some embodiments, prior to introduction of the cells into the subject, the subject may be pre-treated to enhance engraftment of the processed, administered collected cord blood cells provided herein. For example, the subject may be pretreated to enhance self-renewal and/or differentiation of the infused cells, such as, for example, by DPP4 inhibition and/or by preconditioning the subject in a hyperbaric chamber. In another embodiment, prior to introduction of the cells into the subject, the cord blood-derived HSCs may be processed and the subject may be pre-treated to enhance engraftment of the processed, administered cold temperature-collected cord blood cells provided herein. For example, it has been shown in animal models that a combination of PGE pre-treatment of cells followed by injection of these cells into hosts treated with sitagliptin (a DPP4 inhibitor) results in improved engraftment above that of either procedure itself.

In other embodiments, the cord-blood derived HSCs introduced to the subject are allogeneic, such as that collected for storage in a public cord blood bank for use for use by someone other than the donor. In an embodiment, the cord-blood derived HSCs introduced to the subject are autologous, such as with collected cells stored in a private/family bank for one's own future use.

Kits for Collection of Cord Blood Having an Increased Number of HSCs

The present disclosure contemplates kits for carrying out the methods provided herein. Such kits typically comprise two or more components required for collection of cord blood under either a chilled environment or at ambient temperature. Components of the kit include, but are not limited to, one or more of compounds, reagents, containers, equipment and instructions for using the kit. Accordingly, the methods described herein may be performed by utilizing pre-packaged kits provided herein.

In an aspect, a kit for collecting cord blood is provided. The kit comprises a vessel for collection of the umbilical cord blood, and instructions for the collection of the cord blood indicating that the cord blood should be immediately collected into the vessel (e.g., a container, or bag), which has been pre-chilled, in one embodiment to about 4° C. In some embodiments, the instructions further indicate that the chilled cord blood should be transported chilled, in one embodiment at about 4° C. In certain embodiments, the instructions further indicate that the chilled cord blood should be processed chilled, in one embodiment at about 4° C. For example, the collected blood may immediately be stored on and then shipped on ice, or in the presence of a cooling composition, such as a gel ice pack, in an insulated container (e.g., polystyrene), as described herein.

Yet in other embodiments, the kit may include one or more of the following: a composition or device for chilling the collected cord blood, for example in one embodiment to about 4° C.; one or more needles and or cannulas for collecting the cord blood; one or more containers for transporting the collected cord blood (e.g., by shipment to a processing facility); and one or more materials for maintaining the collected cord blood (e.g., an anti-coagulant).

Non-limiting embodiments are described by reference to the following examples which are not to be construed as limiting.

Example 1: Materials and Methods

Animals: mice used for most bone marrow (BM) harvests were male and female C57Bl/6J and 4-6 weeks of age. In other embodiments, female, 8-10 week old C57BL/6, Boy/J and C57BL/6J×Boy/J F1 (herein referred to as F1) mice were obtained from the on-site breeding core facility at Indiana University School of Medicine. All animal procedures were approved by the Indiana University Committee on Use and Care of Animals. Animals were maintained under temperature and light-controlled conditions (21-24° C., 12 hour light/dark cycle) and were group housed according to age and sex. Mice were fed ad libitum. Where indicated, BM was flushed from the femurs of C57BL/6 mice either at ambient air conditions or in a hypoxia chamber kept at 3% $O_2$.

Flow cytometry: this was done using an LSRII cytometer (Becton Dickenson, San Diego, CA) and fluorochrome-conjugated antibodies used for mouse BM cell phenotyping. Antibodies used for human phenotyping were anti-lineage cocktail, CD34, CD38, CD45RA, CD90, and CD49f (BD biosciences or eBioscience). For human umbilical cord blood, hematopoietic stem cells (HSCs) were defined as lineage$^-$CD34$^+$CD38$^+$CD45RA$^-$ CD90$^+$CD49f$^+$, multipotent progenitors (MPPs) were defined as lineage$^-$CD34$^+$ CD38$^-$CD45RA$^-$ CD90$^-$CD49f$^-$, and progenitors were defined as lineage$^-$CD34$^+$CD38$^+$. Antibodies used for mouse phenotyping were anti-lineage cocktail, Sca-1, c-Kit, Flk2, CD34, FcγRII/IIIR, and IL-7R (BD biosciences or eBioscience). For mouse bone marrow, long-term (LT)-HSCs were defined as lineage$^-$ Sca-1$^+$ c-Kit$^+$ Flk2$^-$CD34$^-$, short-term (ST)-HSCs were defined as lineage$^-$ Sca-1$^+$ c-Kit$^+$ Flk2$^-$CD34$^+$, multipotential progenitors (MPPs) were defined as lineage$^-$ Sca-1$^+$ c-Kit$^+$ Flk2$^+$CD34$^+$, common myeloid progenitors (CMPs) were defined as lineage$^-$ Sca-1$^-$ c-Kit$^+$ FcγII/IIR$^{lo}$ CD34$^+$, granulocyte-macrophage progenitors (GMPs) were defined as lineage$^-$ sca-1$^-$ c-Kit$^+$ FcγII/IIIR$^{hi}$ CD34$^+$, megakaryocyte-erythrocyte progenitors (MEPs) were defined as lineage$^-$ Sca-1$^-$ c-Kit$^+$ FcγII/IIIR$^-$ CD34$^-$, and common lymphoid progenitors (CLPs) were defined as lineage$^-$ Sca-1$^{lo}$ Flk2$^+$ IL7-R$^+$.

Cell harvests: mouse BM harvest was done in ambient air using the methods known in the art, except that cells were collected and processed at either RT or at 4° C. See, e.g., Mantel C R, O'Leary H A, Chitteti B R, et al. *Enhancing hematopoietic stem cell transplantation efficacy by mitigating oxygen shock*. CELL. 2015; 1553-1565. All solutions, media, and reagents were chilled to 4° C., or left at room temperature (RT). Subsequent procedures such as surface marker staining and fixation and colony assay procedures were done in air 4° C.

Human cord blood was harvested in ambient air at room temperature as reported, except that cells were immediately chilled to 4° C. or left at RT, collected and processed at either RT or 4° C. See, e.g., Hoggatt J, Singh P, Sampath J & Pelus L M. *Prostaglandin e2 enhances hematopoietic stem cell homing, survival, and proliferation*. BLOOD. 2009; 5444-5455. Briefly, collection of cord blood was performed within 5 minutes of placental delivery through a single venipuncture. 20-30 ml of blood was harvested into a 60 cc syringe, inverted 1× to mix, and then divided into a container of 50 ml chilled (4° C.) PBS or 50 ml of RT PBS with heparin (h)(Sigma #h3393) at 1000 units/ml. Collected cells were transported from delivery room to laboratory at either RT or 4° C. After allowing the RT sample to sit for 45-60 minutes, it was chilled to 4° C. All subsequent processing was performed at 4° C. which included mononuclear and lineage$^-$ cell enrichment. Therefore, the only difference between samples was the temperature at time of collection.

Engraftment of NSG mice: for human experiments, lineage$^-$ cells were infused into sub-lethally irradiated (300 cGY) NSG mice.

Colony assays: these were done as previously reported. See, e.g., Mantel C, Messina-Graham S, Moh A, et al. *Mouse hematopoietic cell-targeted stat3 deletion: stem/progenitor cell defects, mitochondrial dysfunction, ROS overproduction, and a rapid aging-like phenotype.* BLOOD. 2012; 2589-2599. Colonies were scored after incubation at 5% $O_2$, 5% $CO_2$ to maximize detectable colony numbers.

Inhibitors, antibodies, and flow cytometry. In certain embodiments, all inhibitors used were from Selleck Chemicals (Houston, TX). All inhibitors were used at the concentrations indicated. Inhibitors were present in all media starting at when the BM was flushed from the mouse femurs. All cells were in the presence of the inhibitor(s) for at least 1 hour prior to use in experiments. The inhibitors were not washed out. However, in the case of the transplantation experiments inhibitors were diluted out while creating the proper cell dose for transplantation. For flow cytometry, HSC were stained at room temperature for 15 minutes with the following antibodies: Lineage cocktail (Lin)-FITC (BioLegend; cat. #133302), ckit-APC-H7 (BD Bioscience; clone #2B8), Sca1-PE/Dazzle™594 (BioLegend; clone #D7), Flt3-APC (BioLegend; clone #A2F10) and CD150-BV421 (BD Bioscience; clone #Q38-480). HSC populations are defined as Lin-Sca1$^+$ ckit$^+$ (LSK) CD150$^+$ (see gating strategy provided in FIG. 1A). CD3-APC-H7 (BD Bioscience; clone #145-2C11), B220-PE-CF594 (BD Bioscience; clone #RA3-6B2), CD11b-BV421 (BD Bioscience; clone #M1/70), CD45.1-FITC (BD Bioscience; clone #A20), CD45.2-APC (BD Bioscience; clone #104) were used for in vivo transplantation to assess donor BM cell engraftment. FACS analysis was performed with a modified BD Bioscience LSRII and FlowJo software (version 7.6.2; TreeStar, WA). The negative portion was determined by using relevant isotype antibody controls.

In vitro colony-forming unit (CFU) assay. Mouse BM cells were seeded in triplicate in 1.0 mL of methylcellulose culture medium (1% methylcellulose) supplement with 30% FBS, 2 mM L-glutamine, 0.1 mM 2-mercaptoethanol, 0.1 mM hemin (Sigma-Aldrich), 5% vol/vol pokeweed mitogen mouse spleen cell conditioned medium and cytokines: 1 U/mL recombinant human erythropoietin (Amgen; Thousand Oaks, CA), 50 ng/mL recombinant mouse SCF (R&D Systems). Plates were incubated at 5% $CO_2$ and lowered 5% $O_2$ in a humidified chamber. The number of colonies was scored at day 7 with an inverted microscope. See, e.g., C. R. Mantel, H. A. O'Leary, B. R. Chitteti et al., *Enhancing Hematopoietic Stem Cell Transplantation Efficacy by Mitigating Oxygen Shock.* CELL 161 (2015) 1553-1565.

In vivo transplantation. F1 mice (CD45.1$^+$CD45.2$^+$) were lethally irradiated (550 cGy, two doses, 24 hours apart) and transplanted with 50,000 antioxidant or vehicle control treated C57BL/6 (CD45.1$^-$CD45.2$^+$) BM cells and 100,000 Boy/J (CD45.1$^+$CD45.2$^-$) BM competitor cells within 24 hours after irradiation. See, e.g., C. R. Mantel, H. A. O'Leary, B. R. Chitteti et al., *Enhancing Hematopoietic Stem Cell Transplantation Efficacy by Mitigating Oxygen Shock.* CELL 161 (2015) 1553-1565. Peripheral blood (PB) was collected at various time points from host animals by submandibular vein bleeds. The blood samples were treated with red blood cell lysis buffer and then washed in PBS+ 0.5% BSA buffer before staining with CD45.1, CD45.2, CD3 (to determine T cells), B220 (to determine B cells) and CD11b (to determine myeloid cells) antibodies as described above. Mice were sacrificed 12 weeks after transplantation then BM cells were stained and analyzed by flow cytometry, but peripheral blood was assessed at 4 and 12 weeks.

Statistical Analysis. Statistical analysis was done using a 2-tailed student t-test or Anova analysis where appropriate. Results are expressed as mean values±standard deviation. P value less than 0.05 (two-tailed Student's t-test) was considered as statistically significant.

Example 2: Collection and Processing of Human Cord Blood Cells at 4° C. Results in Increased Numbers of Phenotypically-Defined HSCs and Progenitors Since the air-induced differentiation effects of EPHOSS on HSCs is a metabolic process, collecting/processing cells at 4° C., rather than at RT, might enhance HSC collection, despite the current thinking in the field that cord blood should be collected and processed at RT to avoid cell damage that may occur at lower temperature or temperatures higher than body temperature.

Collection and processing of mouse BM cells at 4° C., compared to RT, resulted in significant increases in detectable long-term (LT)- and short-term (ST)-HSCs of 2 fold or greater, with no significant changes in multipotential progenitors (MPPs), common myeloid progenitors (CMPs), granulocyte macrophage progenitors (GMPs), megakaryocyte erythroid progenitors (MEPs) or common lymphoid progenitors (CLPs; FIG. 1A).

Control (RT) values for mouse BM cells/femur were 6993±457, 5487±907, 1931±111, 1964±82 for LT-HSCs; 24625±2820, 4062±974, 1058±7, and 1273±105 for ST-HSCs; 55807±2304, 14427±2571, 16549±583, and 11665±1052 for MPPs; 71156±4373, 29475±2424, 33746±4068, and 39160±1925 for CMPs. 208131±9301, 25005±6063, 10503±2012, and 8795±226 for GMPs; 39375±699, 185180±32695, 396630±60650, and 13685±11983 for MEPs; 858±47 for CLPs.

Figure 1B:
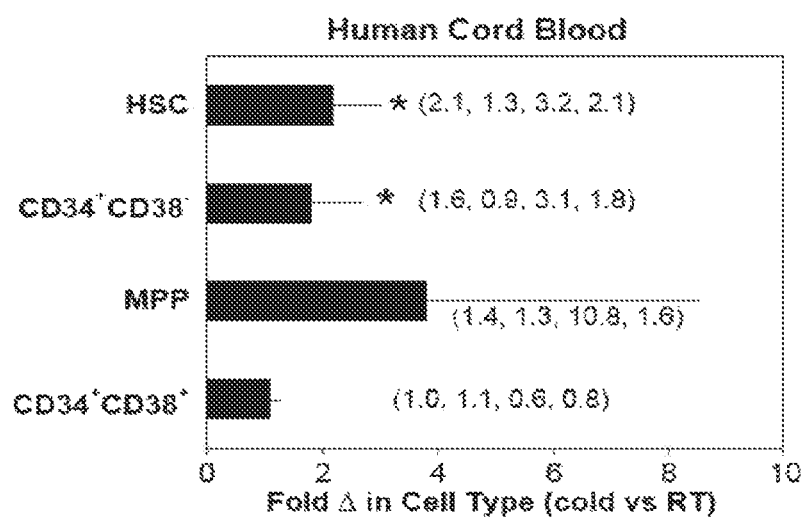
FIG. 1B. Graph illustrating the effects of different temperatures on the level of indicated cells collected from human cord blood. The effects are measured in fold changes; the number of each cell type collected at 4° C. was compared to the number of each cell type collected at RT (room temperature). Results are shown as mean±SEM fold change of absolute numbers for 4 experiments with the individual changes for each experiment shown in parentheses (* $p<0.001$ compared to RT collection and processing).

Collection and processing of human cord blood cells at 4° C., compared to RT, resulted in significant increase of 2 fold in HSCs and in CD34$^+$CD38$^-$ cells, which contain immature subsets of blood cells including HSCs, but with no significant differences detected in MPPs, or in CD34$^+$CD38$^+$ cells, which are enriched for more mature cells, such as progenitors (FIG. 1B). Control (RT) values for cord blood per $10^6$ cells were 468±30, 347±16, 159±7, and 476±36 for HSCs; 2523±139, 2877±194, 1206±42, and 2066±34 for CD34$^+$CD38$^-$ cells; 48±2, 161±14, 128±8, and 322±12 for MPPs; and 4635±42, 5885±591, 6461±122, and 4213±59 for CD34$^+$CD38$^+$ cells.

The enhanced collection of HSCs illustrated in FIGS. 1A and 1B is similar with respect to the increased numbers of HSCs obtained from mouse BM and human cord blood cells that have been collected and processed in hypoxia (e.g., 3% O2) or in ambient air in the presence of cyclosporine A. See, e.g., Mantel C R, O'Leary H A, Chitteti B R, et al. *Enhancing hematopoietic stem cell transplantation efficacy by mitigating oxygen shock.* CELL. 2015; 1553-1565.

Example 3: Collection and Processing of Human Cord Blood Cells at 4° C. Resulted in Decreased Numbers of Functionally-Defined Hematopoietic Progenitor Cells Ambient air-induced differentiation of HSCs can result in decreased numbers of HSCs but increased numbers of functionally assessed HPCs. To test the number of functional HPCs in the cord blood collected using the methods provided herein, colony assays were carried out in which one can distinguish granulocyte macrophage (CFU-GM; colony forming units-granulocyte macrophage), erythroid (BFU-E; burst forming units-erythroid), and multipotential (CFU-GEMM; colony forming units-granulocyte, erythroid, macrophage, megakaryocyte) progenitor cells.

Figure 2A:
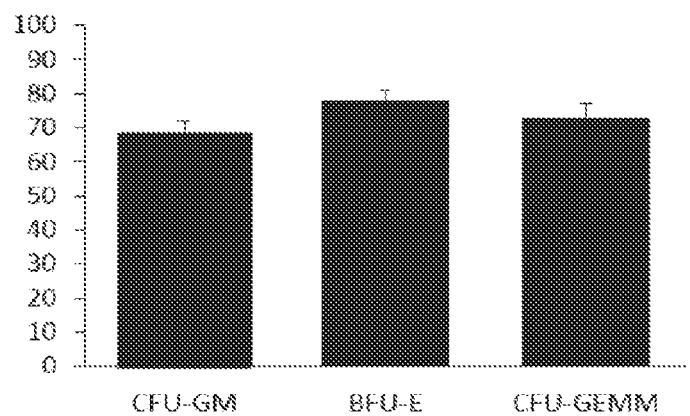
FIG. 2A. Graph illustrating percent decrease in mouse bone marrow hematopoietic progenitor cells (e.g., CFU-GM, BFU-E, and CFU-GEMM) collected at 4° C. when compared to the number of corresponding type of hematopoietic progenitor cells collected at RT. Results are expressed as mean±1 SEM for 4 experiments each. All decreases are significant to at least $p<0.001$.

Collection and processing of mouse BM cells at 4° C., compared to RT, resulted in decreased numbers of functionally detectable HPCs (FIG. 2A). Control numbers of colonies (room temperature, RT) for mouse BM cells/femur (in thousands) were 15.4±3.8, 52.1±8.2, 61.6±9.6, and 3.8±1.9 for CFU-GM; 0.4±0.03, 3.7±1.8, 3.9±1.8, and 2.9±0.2 for BFU-E; and 0.4±0.02, 2.3±0.4, 1.9±0.8, and 0.9±0.1 for CFU-GEMM.

Figure 2B:
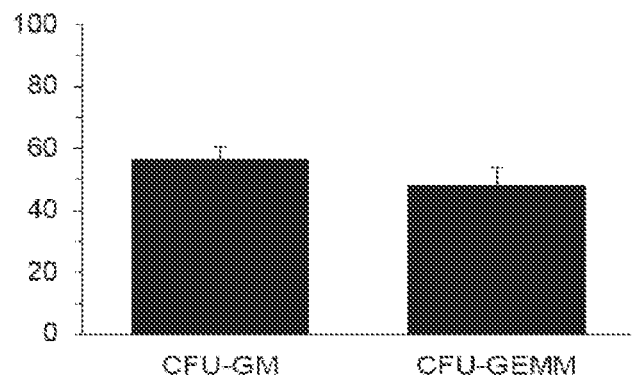
FIG. 2B. Graph illustrating percent decrease in human cord blood hematopoietic progenitor cells (e.g., CFU-GM and CFU-GEMM) collected at 4° C. when compared to the number of corresponding type of hematopoietic progenitor cells collected at RT. Results are expressed as mean±1 SEM for 4 experiments each. All decreases are significant to at least $p<0.001$.

Collection and processing of human cord blood cells at 4° C., compared to RT, resulted in decreased numbers of functionally detectable HPCs (FIG. 2B). Control numbers of colonies (RT) for human cord blood collected at RT were 67±3, 100±6, 34±2, and 38±3 for CFU-GM, and 58±2, 84±5, 69±2, and 37±2 for CFU-GEMM per $2.5 \times 10^4$ low density cord blood cells plated/ml (* p<0.001 compared to RT controls).

The enhanced collection of HSCs containing decreased numbers of functionally detectable HPCs illustrated in FIGS. 2A and 2B is similar with respect to the decreased numbers of HSCs obtained from mouse BM and human cord blood cells that have been collected and processed in hypoxia (e.g. 3% O2) or in ambient air in the presence of cyclosporine A.

Figure 3A:
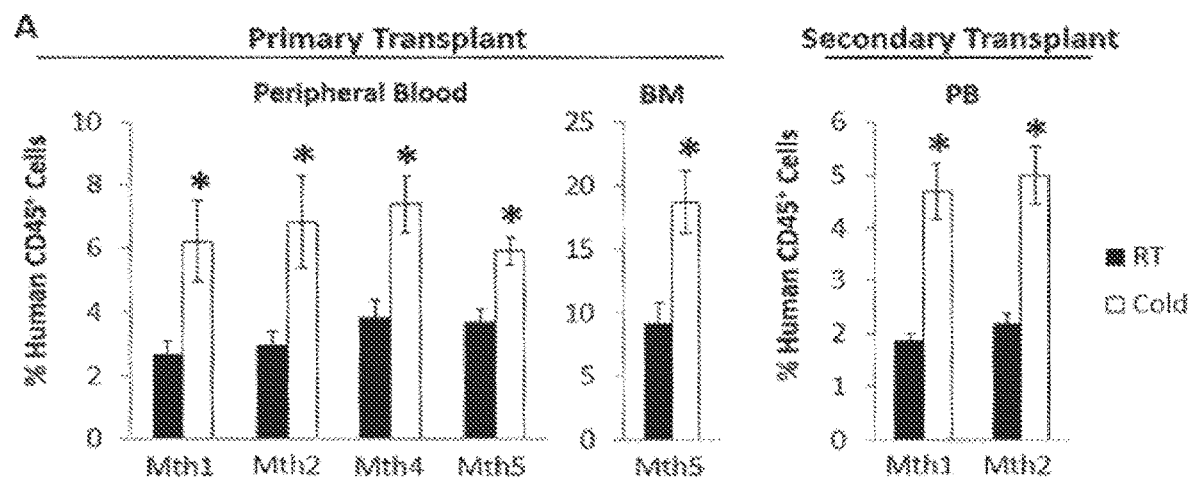
FIG. 3A. Graphs illustrating percent human $CD45^+$ cells in the peripheral blood and bone marrow of sub-lethally irradiated immune deficient NSG mice at indicated time points (Mth: month) after the primary and/or secondary transplants. Data are average±SEM.*, indicates a $p<0.05$ when compared to RT group.

Example 4: Collection and Processing of Human Cord Blood Cells at 4° C. Resulted in Improved In Vivo Engraftment of Cells To assess the capacity for in vivo human engraftment of HSCs generated using the methods provided herein, both short- and long-term, a sub-lethally-irradiated immune deficient mouse model, NSG, was used. For primary transplantations, NSG mice were infused with $1 \times 10^5$ human cord blood lineage negative cells that were collected and processed either at 4° C. or at RT. See, e.g., Mantel C R, O'Leary H A, Chitteti B R, et al. *Enhancing hematopoietic stem cell transplantation efficacy by mitigating oxygen shock.* CELL. 2015; 1553-1565. The percent of human $CD45^+$ cells in the peripheral blood (PB) and bone marrow (BM) was determined by flow cytometry at the indicated time points (FIG. 3A, "Mth" refers to month). For secondary transplants, sub-lethally irradiated NSG mice received $2 \times 10^6$ BM cells from primary-recipient NSG mice then the percent human $CD45^+$ cells in the PB was determined (FIG. 3A).

Figure 3B:
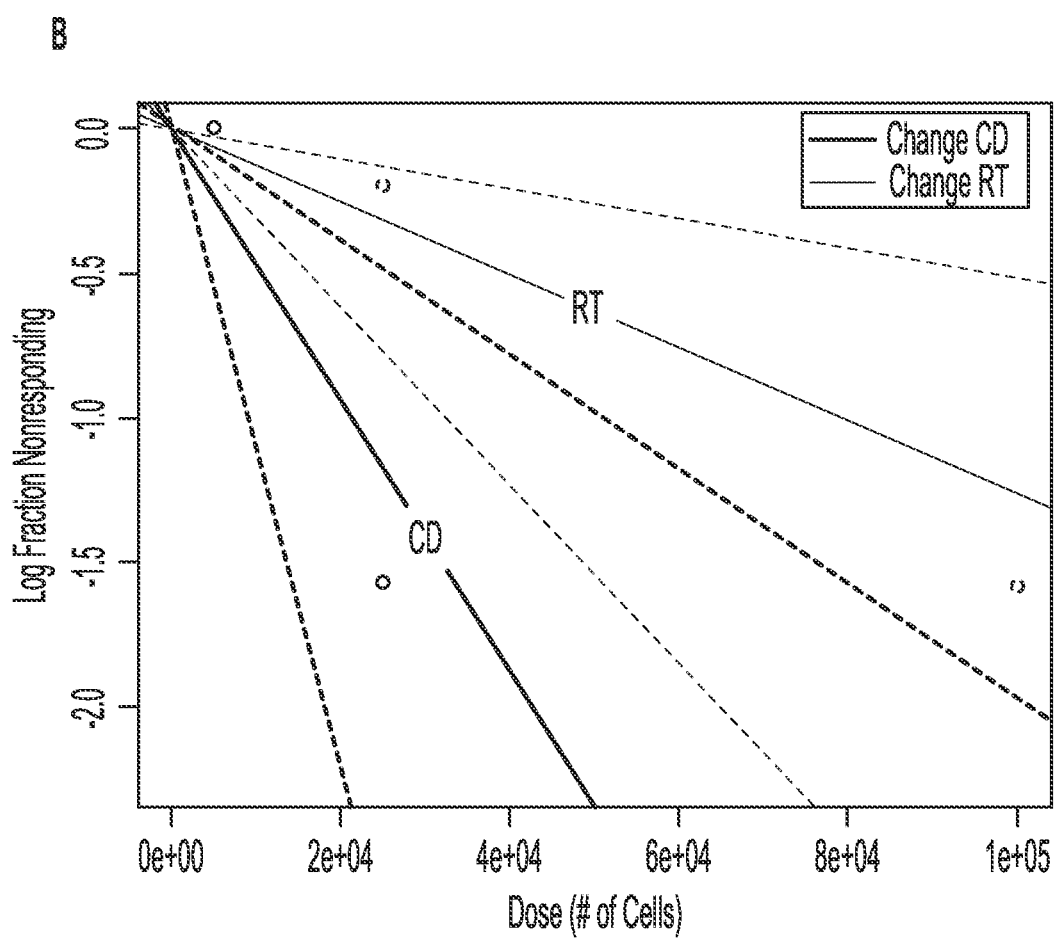
FIG. 3B. Graph illustrating limited dilution analysis of engrafting HSCs by assessing non-responding cells.
Figure 3C:
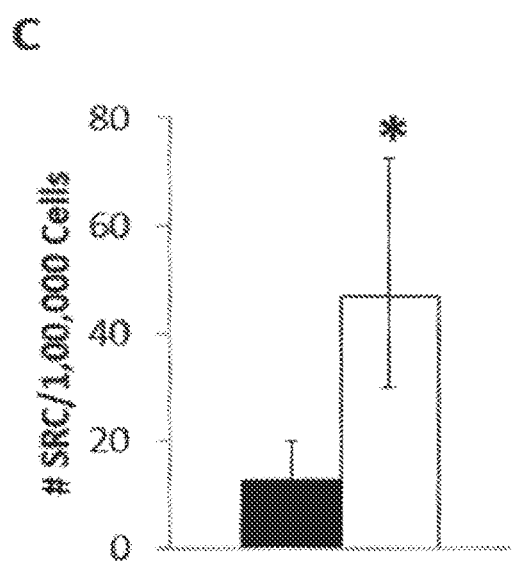
FIG. 3C. Graph illustrating the number of SCID repopulating cells (SRCs; which quantifies numbers of functional human HSCs based on the limited dilution analysis shown in FIG. 3B). Data are average±SEM.*, indicates a p<0.05 when compared to RT group.

To determine the frequency of SCID repopulating cells (SRCs) from the cords collected/processed under different temperatures, limited dilution assays were performed where $5 \times 10^3$, $2.5 \times 10^4$ or $1 \times 10^5$ human cord blood lineage negative cells collected/processed either under cold or RT conditions were infused into sub-lethally irradiated NSG mice. After 5 months the percent human $CD45^+$ cells in the bone marrow was determined by flow cytometry. Poisson statistical analysis of this transplant was performed and the percentage of mice with less than 5% human $CD45^+$ cells in the BM versus the dose of cells transplanted was plotted. The RT and cold (CD) groups are noted in FIG. 3B. The solid lines indicate the best fit linear model for each data set. Dotted lines represent 95% confidence intervals. Data was plotted using ELDA software (FIG. 3B). The number of SRC was calculated using L-Calc software. N=5 mice per group for primary transplant experiments (FIG. 3C). N=10 mice per group for secondary transplant experiments. Data are average±SEM.*, indicates a p<0.05 when compared to RT group. The human cord blood cells collected/processed at 4° C. engrafted sub-lethally-irradiated NSG mice significantly better than those cells collected/processed at RT.

Hence, collection/processing of cells in ambient air at 4° C., compared to that at RT, significantly enhances the numbers of HSCs collected in a more easily performed, less time-consuming process that is more cost efficient relative to known methods for enhancing the number of HSCs in collected cord blood.

Example 5: Combinations of Antioxidants Increased the Numbers of Collected HSCs in Ambient Air The only environmental difference between "hypoxia harvest" (e.g., harvest of cord blood under 3% $O_2$) and "normoxia harvest" (harvest of cord blood under ambient air) is the oxygen level. Antioxidants, which inhibit the oxidation of molecules, may be able to reverse the effect of oxidative stress on HSCs induced by EPHOSS. Mouse bone marrow cells were collected in ambient air, but in the absence and presence of different compounds to attempt to mimic the effects of "hypoxia harvest" on HSCs, and then compared these combinations with collection in either hypoxia or in air at 4° C.

Hypoxic bone marrow harvest was done in a custom-configured, temperature-, humidity-, $O_2$-, and $CO_2$-controlled glove box (Hypoxic Chamber, Coy) routinely maintained at 3% $O_2$, 5% $CO_2$, and $N_2$ balance. After sacrifice, animals were immediately transferred into the hypoxia chamber through a gassed air lock where femurs were obtained and flushed. All solutions, reagents, and plastic ware and pipet tips, and sterile gauze, as well as anything that could come into contact with either the femur or the flushed BM cells, were pre-equilibrated in the hypoxic chamber for at least 18 hours prior to use. Subsequent procedures such as surface marker staining and fixation and colony assay procedures were done inside the chamber.

Flow cytometry was done using an LSRII cytometer (Becton Dickenson) and fluorochrome-conjugated antibodies used for mouse BM cell phenotyping. Antibodies used for mouse phenotyping includes anti-lineage cocktail, c-kit, Scl-1, Flt-3, CD150 (BD biosciences). Long-Term (LT)-engrafting HSCs are defined as $Lin^-$ $c-kit^+$ $Sca-1^+$ $Flt-3^+$ $CD150^+$.

Colony assays were done as reported. Colonies were scored after incubation at 5% $O_2$, 5% $CO_2$ to maximize detectable colony numbers.

Mouse bone marrow cells were collected and processed with 1 mM N-Acetyl-Cysteine (NAC) in ambient air. NAC is a classic antioxidant which has been proven to be useful in many oxidative stress studies. See, e.g., Tothova Z, Kollipara R, Huntly B J, et al. *FoxOs are critical mediators of hematopoietic stem cell resistance to physiologic oxidative stress.* CELL. 2007; 128: 325-39. However, there was no significant change in numbers of collected HSCs in ambient air in the presence of NAC (FIG. 4A, 4B). A higher dose of NAC (3 mM) was tested, with no increase in numbers of collected HSCs. NAC was then combined with another antioxidant, ascorbic acid 2-phosphate (AAP) to evaluate the protection and increased numbers of HSC collected in ambient air under the stress of EPHOSS. Co-treatment with 1 mM NAC and 0.22 mM AAP, but not AAP alone, significantly increased numbers of HSC from 99±6 per million BMCs to 208±17 per million BMCs (p<0.001), which is similar to the number of HSC collected in the hypoxia chamber: 235±25 per million BMCs (FIG. 4A, 4B). In accord, enhanced recovery of HSCs by combinatory antioxidant treatment resulted in decreased numbers of the granulocyte-macrophage (CFU-GM) and erythroid (BFU-E) progenitor cells equivalent to the cell numbers collected in hypoxia alone or in combination of antioxidants demonstrating decreased differentiation of HSCs in this condition.

Example 6: Combinations of Epigenetic Inhibitors Increased the Numbers of Collected HSCs in Ambient Air A small-scale epigenetic inhibitor library screen was conducted to test whether selected epigenetic inhibitors can reverse the EPHOSS-induced HSC cell loss. s1451 is an inhibitor of Aurora kinase. s2821 is an inhibitor of DNA methyltransferase. s1060 is an inhibitor of PARP1/2. Referring now to FIG. 5A, combinatory treatment for cell collection in ambient air with s1451+s2821 or s1451+s1060 significantly increased numbers of collected HSCs in air (2.1 to 2.3 fold change). Referring now to FIG. 5B-D, the combination of other inhibitors of Aurora kinase (s1103, s1147) with other inhibitors of DNA methyltransferase (s1200, s1782), or other inhibitors of PARP1/2 (s1004, s2886) also increased HSC cell number significantly. Thus, using combinations of antioxidants, or an inhibitor of Aurora kinase with either an inhibitor of DNA methyltransferase, or of PARP1/2 enhanced collections of mouse bone marrow HSCs in the presence of ambient air, that equated with the numbers of these cells collected in hypoxia.

Figure 5E:
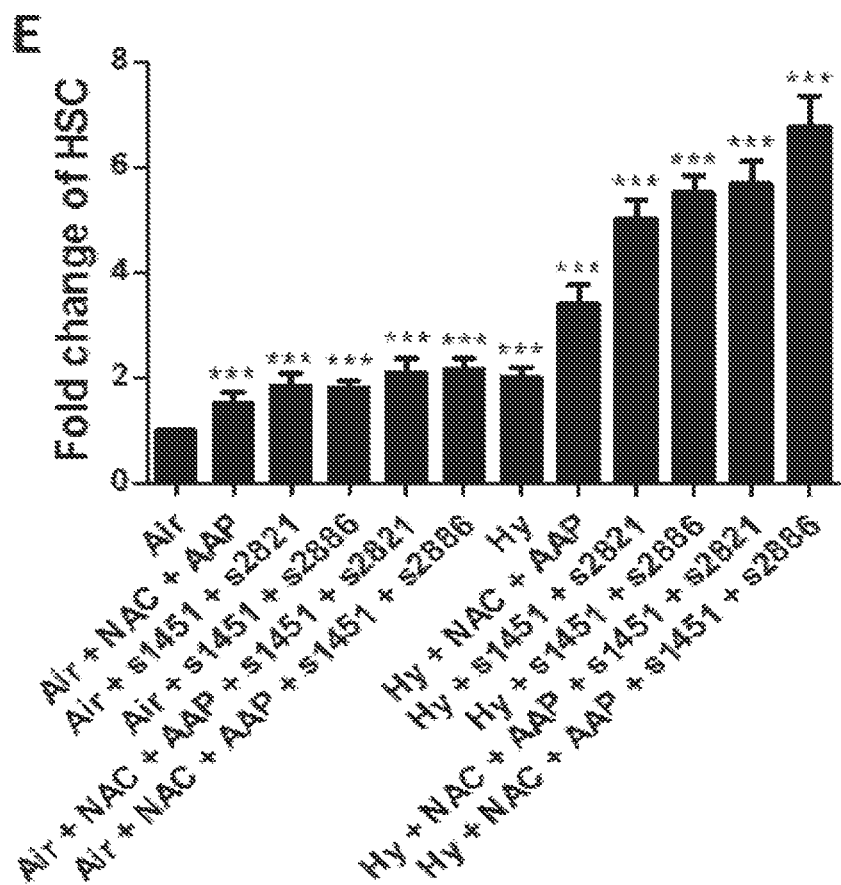
FIG. 5E. Graph illustrating the effect of antioxidants and/or epigenetic inhibitors on the number of mouse bone marrow HSCs. The fold change of mouse bone marrow HSCs collected in ambient air or in hypoxia (about 3% $O_2$) in the presence of 1 mM NAC, 0.22 mM AAP, 10 μM s1451 (Aurora kinase inhibitor), 10 μM s2821 (DNA methyltransferase inhibitor), and/or 10 μM s2886 (PARP1/2 inhibitor) is shown. * p<0.05,  p<0.01, * p<0.001. n=3, 7 mice.

Referring now to FIG. 5E, combinatory epigenetic inhibitor treatment for cells collected in the hypoxia chamber (performed as described in Example 5) also showed dramatic increases of HSCs compared to the numbers of HSCs collected in hypoxia without these reagents. Thus, further enhanced collection of HSCs can be achieved by hypoxic collection plus use of epigenetic inhibitors.

Figure 6:
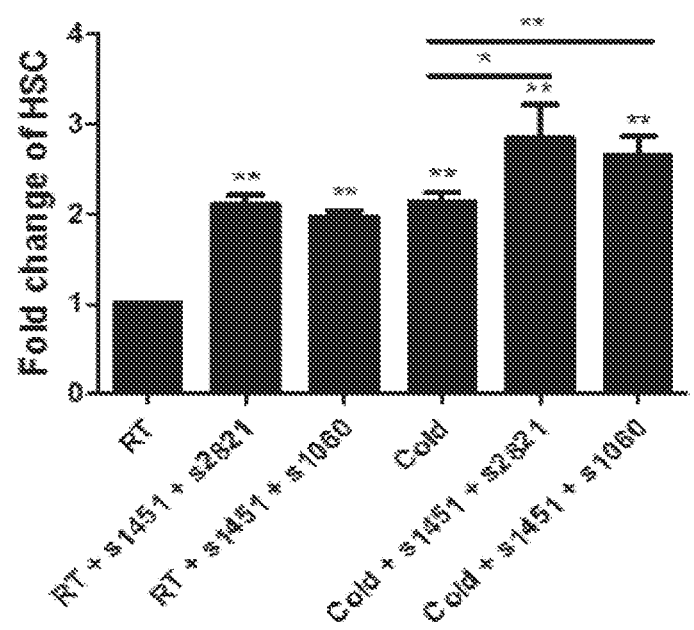
FIG. 6. Graph illustrating the effect of epigenetic inhibitors on the number of mouse bone marrow HSCs. The fold change of mouse bone marrow HSCs collected in ambient air at room temperature (RT) or on ice (Cold) in the presence of 10 μM s1451 (Aurora kinase inhibitor), 10 μM s2821 (DNA methyltransferase inhibitor), and/or 10 μM s1060 (PARP1/2 inhibitor) is shown. Cells were collected and processed in the presence of inhibitors at RT or on ice for 1 hour. Then cells were stained with HSC markers at room temperature for 15 minutes. * p<0.05,  p<0.01, * p<0.001. n=3, 4 mice.

The effect of collecting mouse bone marrow cells in cold (about 4° C.) temperatures, rather than in hypoxia at room temperature, but in the absence and presence of epigenetic inhibition was also evaluated. Referring now to FIG. 6, greater numbers of mouse bone marrow HSCs were collected in ambient air at 4° C. than at room temperature, and the addition of combinations of the epigenetic inhibitor to the cold collected cells statistically enhanced the collection of HSCs even further.

Example 7: Combination Antioxidant Treatment Mimics 'Hypoxia Harvest'

As noted above, an environmental difference between 'hypoxia harvest' and 'normoxia (ambient air collected) harvest' is the oxygen level. Antioxidants, which inhibit the oxidation of molecules, can prevent the effect of oxidative stress on HSCs induced by EPHOSS.

Referring now to FIG. 7, Bone marrow cells were harvested and processed in a hypoxic chamber. Groups exposed to air were removed from the chamber and placed in ambient air for 60 minutes. Mouse BM cells were collected with 1 mM N-Acetyl-Cysteine (NAC), a classic antioxidant which has been proven to be useful in many oxidative stress studies, in the flush media collected in ambient air. Cells were incubated with the inhibitor for 1 hour and remained in all media for the rest of the experiment. In this system, there was no significant change in numbers of collected HSC in ambient air in the presence of 1 mM NAC (FIG. 7B-C). A higher dose of NAC (3 mM) was tested, with no increase in numbers of collected HSCs (data not shown). Another antioxidant, ascorbic acid 2-phosphate (AAP), is added to check whether this antioxidant, alone or in combination with NAC, could produce protection and increased numbers of HSCs collected in ambient air under the stress of EPHOSS. Co-treatment with 1 mM NAC and 0.22 mM AAP, but not AAP alone, significantly increased numbers of HSCs from 99±6 per million BM cells to 208±17 per million BM cells ($p<0.001$), which is similar to the number of HSC collected in the hypoxia chamber without these added reagents: 235±25 per million BM cells (FIG. 7A-C).

To check whether antioxidant treatment influenced HPC numbers, mouse BM cells treated with either antioxidants or vehicle control were seeded in methylcellulose medium and cultured for 7 days in the presence of cytokines. Referring now to FIG. 7D-F, combination antioxidant treatment resulted in significantly decreased numbers of granulocyte/macrophage (CFU-GM), erythroid (BFU-E), and granulocyte/erythrocyte/macrophage/megakaryocyte (CFU-GEMM) progenitors, demonstrating that combination antioxidant treatment produces the same decrease in progenitor cell numbers as does hypoxia collection and processing (FIG. 7D-F).

Example 8: Antioxidant Treatment Enhances HSC Engraftment

To test the functional significance of antioxidant treatment on HSCs, lethally irradiated F1 mice were transplanted with C57BL/6 BM cells treated with antioxidant combination or vehicle control, and competitive Boy/J BM cells.

Referring now to FIG. 8, 50000 antioxidant or vehicle control treated CD45.2$^+$ C57BL/6 mouse bone marrow cells and 100000 CD45.1$^+$ Boy/J competitive cells were infused into lethally irradiated dual CD45.2$^+$/CD45.1$^+$ F1 recipients. Data was collected 1 and 3 months after injection. Significantly increased engraftment in PB at 1 and 3 months and BM at 3 months post donor cell infusion was observed in the combination antioxidant treated group, compared to the vehicle control group (FIG. 8A-B), consistent with previously published findings of enhanced engraftment when using hypoxia collected and processed mouse BM cells. See, e.g., C. R. Mantel, H. A. O'Leary, B. R. Chitteti et al., *Enhancing Hematopoietic Stem Cell Transplantation Efficacy by Mitigating Oxygen Shock.* CELL, 161 (2015); 1553-1565. The increased chimerism of the antioxidant treated cells was apparent for B cells, T cells and myeloid cells (FIG. 8C-E).

Example 9: Epigenetic Enzyme Inhibitor Treatment Mimics and Expands on Hypoxia Harvest The possibility of chromatin remodeling and/or epigenetic change(s) during EPHOSS was considered and a small-scale epigenetic inhibitor library screen was conducted to test whether selected epigenetic inhibitors could prevent the EPHOSS-induced HSC cell loss. Aurora A Inhibitor I (s1451) is an inhibitor of Aurora kinase. RG108 (s2821), is an inhibitor of DNA methyltransferase. Olaparib (s1060) is an inhibitor of PARP1/2. Referring now to FIG. 9A, combinatory inhibitor treatment (with inhibitors in all media from flush through experimental processing) for cell collection in ambient air with 10 μM s1451+10 μM s2821, or 10 μM s1451+10 μM s1060 significantly increased numbers of collected HSCs in air (2.1 to 2.3 fold change; FIG. 9A). Referring now to FIG. 9B-D, the combination of other inhibitors of Aurora kinase (s1103 and/or s1147; 10 μM)

with other inhibitors of DNA methyltransferase (s1200 and/or s1782; 10 µM), or other inhibitors of PARP1/2 (s1004s and/or s2886; 10 µM) also significantly increased HSC numbers. Thus, using combinations of antioxidants, or an inhibitor of Aurora kinase with either an inhibitor of DNA methyltransferase, or of PARP1/2 enhanced collections of mouse BM HSC in the presence of ambient air resulted in numbers that equated with those cells collected in hypoxia.

Figure 9E:
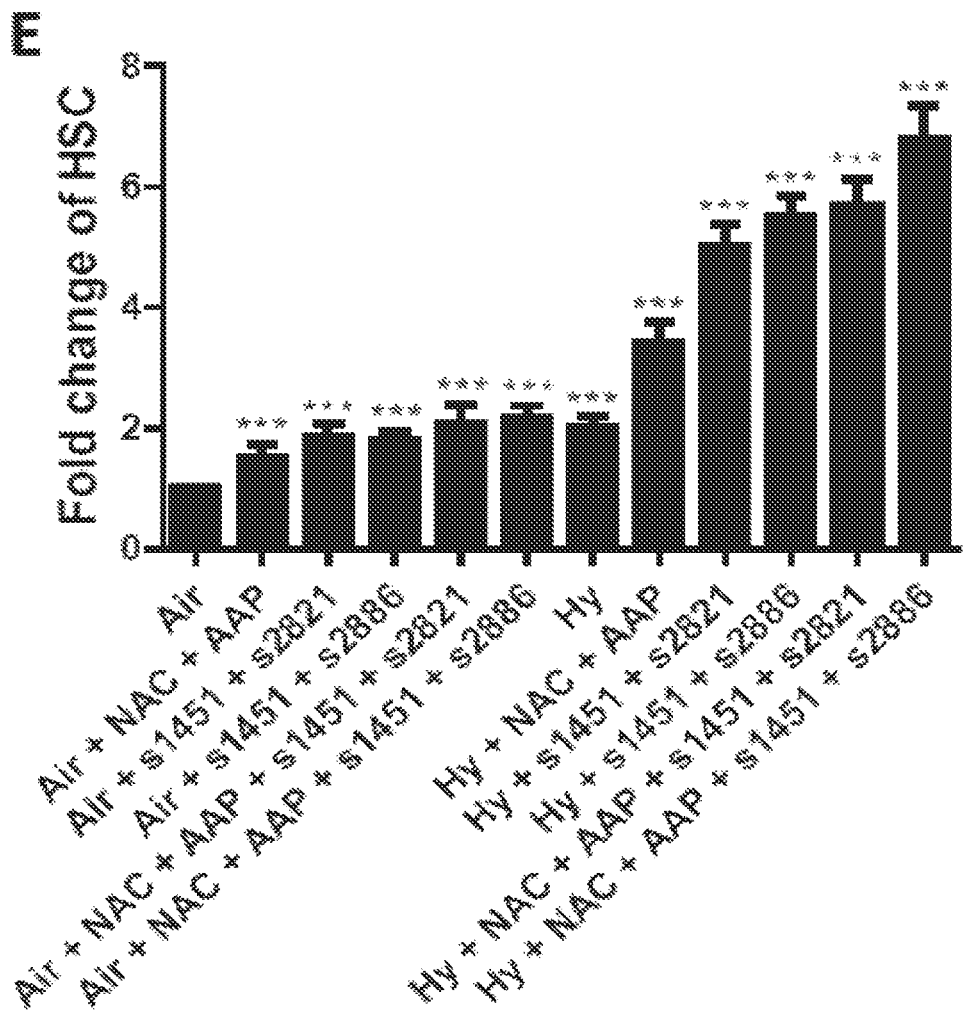
FIG. 9E. Graph illustrating the effect of antioxidants and/or epigenetic inhibitors on the number of mouse bone marrow HSCs. The fold change of mouse bone marrow HSCs collected in ambient air or in hypoxia (about 3% O$_2$) in the presence of 1 mM NAC, 0.22 mM AAP, 10 μM s1451 (Aurora kinase inhibitor), 10 μM s2821 (DNA methyltransferase inhibitor), and/or 10 μM s2886 (PARP1/2 inhibitor) is shown. * p<0.05,  p<0.01, * p<0.001. n=3, 7 mice.

Furthermore, combinatory inhibitor treatment for cells collected in the hypoxia chamber also showed dramatic increases of HSC compared to the numbers of HSCs collected in hypoxia without these reagents (FIG. 9E). Thus, a number of different means to further enhance collection of HSCs even during hypoxic collection of the BM cells has been identified.

Previous studies have shown that brief exposure of mouse bone marrow cells to air limits the efficiency of HSC recovery. In this Example, based on the fact that the only difference between "normoxia harvest" and "hypoxia harvest" is the oxygen level, several antioxidants and their combinations were tested and found using in vitro and in vivo assays that the antioxidant combination NAC+AAP mimics the HSC recovery typically seen in "hypoxia harvest."

Epigenetic enzymatic regulators were evaluated by conducting a small-scale epigenetic enzyme inhibitor library screen, and found that some combinations of epigenetic enzyme inhibitors could also mitigate the apparent EPHOSS-induced HSC differentiation in air.

Hematopoietic stem cell transplantation (HCT), especially with cord blood (CB), is limited to a degree by the numbers of HSCs found in single CB collections. Means to enhance the collection of HSCs could have significant therapeutic effect. The Examples provided herein clearly demonstrate that the instant inventors have identified improved means for enhancing the collection of HSCs from cord blood, peripheral blood and bone marrow.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

We claim:

1. A method for generating a population of hematopoietic stem cells capable of engraftment, comprising:
   harvesting a portion of cells from bone marrow, umbilical cord blood, and/or peripheral blood of a subject in ambient air;
   transferring the harvested cells directly into a chilled collection environment of about 1.5-5° C., wherein chilled phosphate buffered saline (PBS) with heparin is present in the chilled collection environment at the time of transfer or immediately after the transfer;
   processing the harvested cells to generate a population of hematopoietic stem cells, wherein the harvested cells are maintained at temperatures of about 1.5-5° C. throughout processing.

2. The method according to claim 1, wherein the step of transferring occurs at a temperature from about 1° C. to about 5° C., from about 2° C. to about 4° C., from about 3° C. to about 4° C., about 1° C., about 2° C., about 3 C, about 4° C., about 5° C., or any combination thereof.

3. The method according to claim 1, wherein the step of harvesting occurs at a temperature from about 16° C. to about 25° C., from about 18° C. to about 23° C., from about 20° C. to about 22° C., about 18° C., about 19° C., about 20° C., about 21° C., about 22° C., or any combination thereof.

4. The method of claim 1, where the transferring step includes exposing the harvested cells to two antioxidants, two epigenetic inhibitors, or one antioxidant and one epigenetic inhibitor.

5. The method of claim 4, where at least one of the antioxidants is selected from the group consisting of: n-acetyl-cysteine, thiols, vitamin A, vitamin C, vitamin E, uric acids, melatonin, glutathione, and ascorbic acid 2-phosphate.

6. The method of claim 4, where at least one of the epigenetic inhibitors is an agent capable of inhibiting one of the activities selected from the following: DNA methylation, histone deacetylation, and histone acetylation.

7. The method of claim 4, wherein the epigenetic inhibitor is selected from the group consisting of: a DNA methyltransferase inhibitor, an Aurora kinase inhibitor, and a PARP1/2 inhibitor.

* * * * *